United States Patent
Lee

(10) Patent No.: US 9,859,501 B2
(45) Date of Patent: *Jan. 2, 2018

(54) ORGANIC COMPOUND AND ORGANIC LIGHT EMITTING DIODE DEVICE INCLUDING THE SAME

(71) Applicant: SAMSUNG DISPLAY CO., LTD., Yongin, Gyeonggi-Do (KR)

(72) Inventor: Jung-Sub Lee, Yongin (KR)

(73) Assignee: Samsung Display Co., Ltd., Yongin, Gyeonggi-do (KR)

( * ) Notice: Subject to any disclaimer, the term of this patent is extended or adjusted under 35 U.S.C. 154(b) by 778 days.

This patent is subject to a terminal disclaimer.

(21) Appl. No.: 14/284,484

(22) Filed: May 22, 2014

(65) Prior Publication Data

US 2015/0048327 A1    Feb. 19, 2015

(30) Foreign Application Priority Data

Aug. 14, 2013 (KR) .......................... 10-2013-0096832

(51) Int. Cl.
*H01L 51/00* (2006.01)
*C09K 11/06* (2006.01)
(Continued)

(52) U.S. Cl.
CPC ........ *H01L 51/0058* (2013.01); *C07C 211/61* (2013.01); *C09K 11/06* (2013.01);
(Continued)

(58) Field of Classification Search
CPC ............... C07C 211/61; H01L 51/0058; H01L 51/0059; H01L 51/006; H01L 51/0081; H01L 51/5056; C09K 11/06
See application file for complete search history.

(56) References Cited

U.S. PATENT DOCUMENTS 9,543,525 B2 *  1/2017  Jeong ................. H01L 51/0058
2003/0118866 A1 *  6/2003  Oh ........................ H01L 51/006
428/690

(Continued)

FOREIGN PATENT DOCUMENTS

JP       2009-046482 A    3/2009
KR    10-2006-0071461 A    6/2006
(Continued)

OTHER PUBLICATIONS

Helvetica Chimica Acta (1973), 56(8), pp. 3044-3049.*

*Primary Examiner* — Dawn Garrett
(74) *Attorney, Agent, or Firm* — Lee & Morse, P.C.

(57) ABSTRACT

A compound is represented by the following Chemical Formula 1:

[Chemical Formula 1]

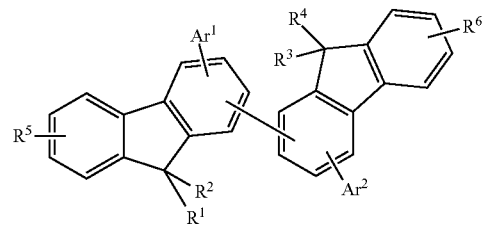

wherein, in the above Chemical Formula 1, $R^1$ to $R^6$ and $Ar^1$ to $Ar^2$ are as defined in the specification.

11 Claims, 2 Drawing Sheets

(51) Int. Cl.
*C07C 211/61* (2006.01)
*H01L 51/50* (2006.01)

(52) U.S. Cl.
CPC ........ *H01L 51/006* (2013.01); *H01L 51/0059* (2013.01); *H01L 51/0081* (2013.01); *H01L 51/5056* (2013.01)

(56) References Cited

U.S. PATENT DOCUMENTS

| | | | |
|---|---|---|---|
| 2003/0219625 A1* | 11/2003 | Wolk | C09K 11/06 428/690 |
| 2004/0110958 A1 | 6/2004 | Nishiyama et al. | |
| 2008/0142790 A1* | 6/2008 | Kitamura | C09B 47/0671 257/40 |
| 2008/0200736 A1* | 8/2008 | Kosuge | C07C 13/567 585/26 |
| 2009/0033211 A1* | 2/2009 | Tanabe | C09K 11/06 313/504 |
| 2010/0072885 A1* | 3/2010 | Watanabe | C07C 13/567 313/504 |
| 2012/0080585 A1* | 4/2012 | Fukuzaki | B82Y 10/00 250/214.1 |

FOREIGN PATENT DOCUMENTS

| | | |
|---|---|---|
| KR | 10-2007-0091183 A | 9/2007 |
| KR | 10-2010-0106626 A | 10/2010 |
| WO | WO 2006-073054 A1 | 7/2006 |

* cited by examiner

ORGANIC COMPOUND AND ORGANIC LIGHT EMITTING DIODE DEVICE INCLUDING THE SAME

CROSS-REFERENCE TO RELATED APPLICATION

Korean Patent Application No. 10-2013-0096832, filed on Aug. 14, 2013, in the Korean Intellectual Property Office, and entitled: "Organic Compound and Organic Light Emitting Diode Device Including The Same," is incorporated by reference herein in its entirety.

BACKGROUND

Embodiments relate to an organic compound and an organic light emitting diode device including the same.

SUMMARY

Embodiments are directed to a compound represented by the following Chemical Formula 1:

[Chemical Formula 1]

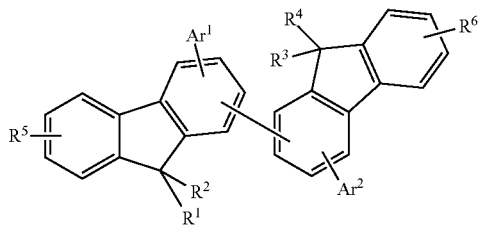

wherein, in the above Chemical Formula 1, $R^1$ to $R^6$ are each independently hydrogen, deuterium, a halogen, a substituted or unsubstituted C1 to C30 alkyl group, a substituted or unsubstituted C2 to C30 alkenyl group, a substituted or unsubstituted C2 to C30 alkynyl group, a substituted or unsubstituted C3 to C30 cycloalkyl group, a substituted or unsubstituted C1 to C30 alkoxy group, a substituted or unsubstituted C6 to C30 aryloxy group, a substituted or unsubstituted C6 to C30 arylthiol group, a substituted or unsubstituted C6 to C30 aryl group, a substituted or unsubstituted C2 to C30 heteroaryl group, a substituted or unsubstituted C1 to C30 amine group, a substituted or unsubstituted silyl group, a cyano group, a nitro group, a hydroxy group, a carboxyl group, or a combination thereof, and $Ar^1$ and $Ar^2$ are each independently hydrogen, deuterium, a halogen, a substituted or unsubstituted C1 to C30 alkyl group, a substituted or unsubstituted C6 to C30 aryl group, a substituted or unsubstituted C2 to C30 heteroaryl group, a substituted or unsubstituted C1 to C30 amine group, or a combination thereof.

The compound represented by the above Chemical Formula 1 may be a compound represented by the following Chemical Formula 2:

[Chemical Formula 2]

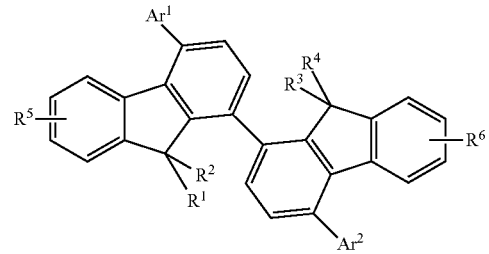

wherein, in the above Chemical Formula 2, $R^1$ to $R^6$ are each independently hydrogen, deuterium, a halogen, a substituted or unsubstituted C1 to C30 alkyl group, a substituted or unsubstituted C2 to C30 alkenyl group, a substituted or unsubstituted C2 to C30 alkynyl group, a substituted or unsubstituted C3 to C30 cycloalkyl group, a substituted or unsubstituted C1 to C30 alkoxy group, a substituted or unsubstituted C6 to C30 aryloxy group, a substituted or unsubstituted C6 to C30 arylthiol group, a substituted or unsubstituted C6 to C30 aryl group, a substituted or unsubstituted C2 to C30 heteroaryl group, a substituted or unsubstituted C1 to C30 amine group, a substituted or unsubstituted silyl group, a cyano group, a nitro group, a hydroxy group, a carboxyl group, or a combination thereof, and $Ar^1$ and $Ar^2$ are each independently hydrogen, deuterium, a halogen, a substituted or unsubstituted C1 to C30 alkyl group, a substituted or unsubstituted C6 to C30 aryl group, a substituted or unsubstituted C2 to C30 heteroaryl group, a substituted or unsubstituted C1 to C30 amine group, or a combination thereof.

$Ar^1$ and $Ar^2$ may each independently be a substituted or unsubstituted C1 to C30 amine group.

$Ar^1$ and $Ar^2$ may each independently be a C1 to C30 amine group substituted with an aryl group.

$Ar^1$ and $Ar^2$ may each independently be a C1 to C30 amine group substituted with a substituted or unsubstituted phenyl group, a substituted or unsubstituted biphenyl group, a substituted or unsubstituted naphthyl group, a substituted or unsubstituted anthracenyl group, or a substituted or unsubstituted phenanthrenyl group.

$Ar^1$ and $Ar^2$ may be the same.

$R^1$ to $R^6$ may each independently be a substituted or unsubstituted C1 to C30 alkyl group, a substituted or unsubstituted C6 to C30 aryl group, or a substituted or unsubstituted C2 to C30 heteroaryl group.

$R^1$ to $R^4$ may each independently be a substituted or unsubstituted C1 to C30 alkyl group.

The compound represented by the above Chemical Formula 1 may be at least one of the following compounds 1 to 18:

1

2

3

4

5

6

7
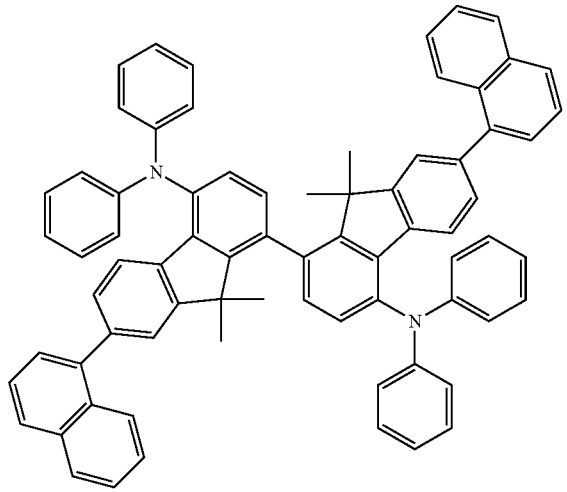
8
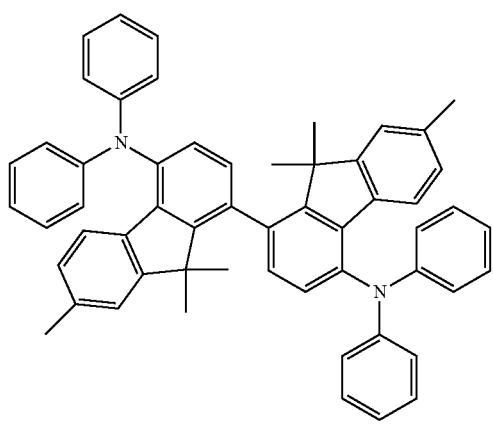
9
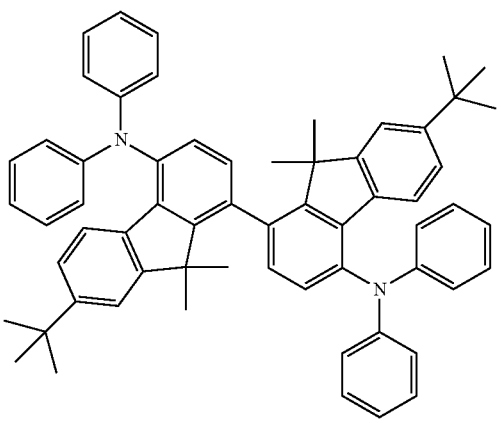
10
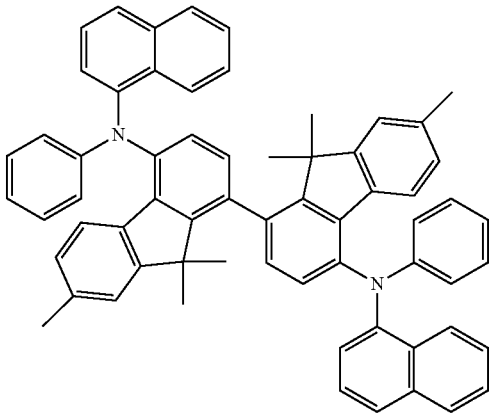
11
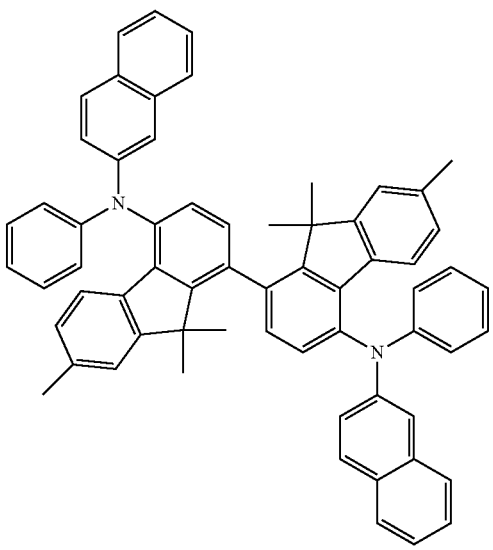
12
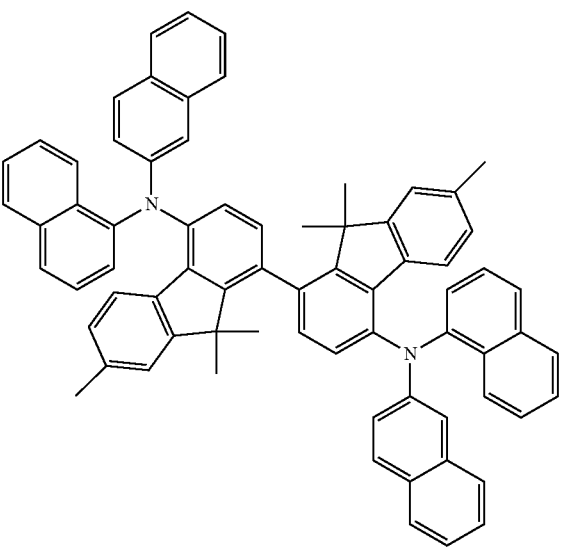

13
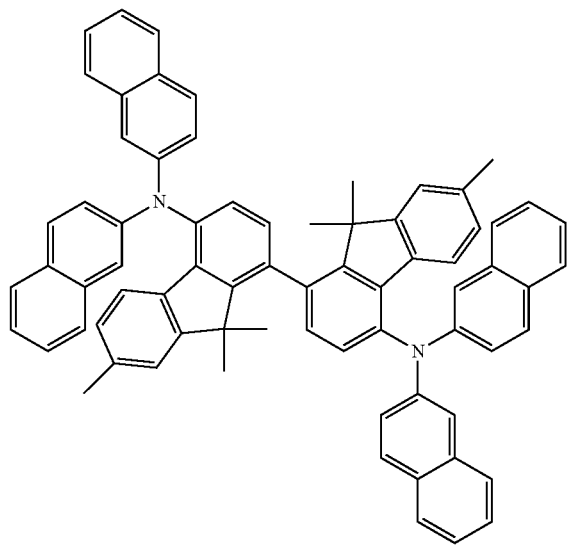
14
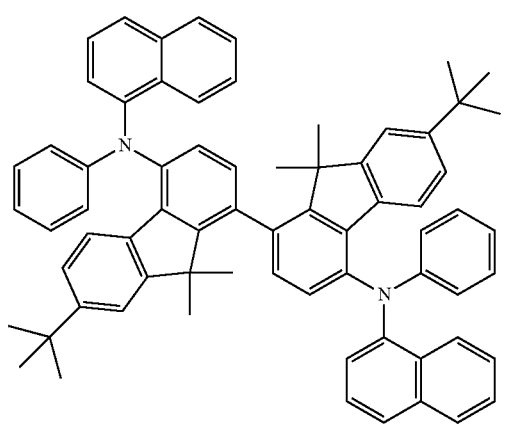
15
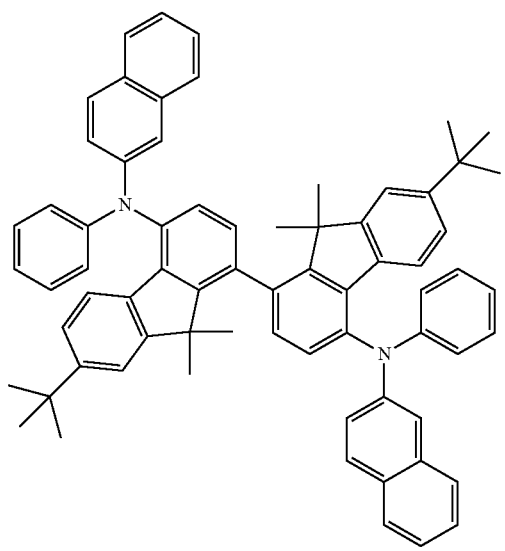
16
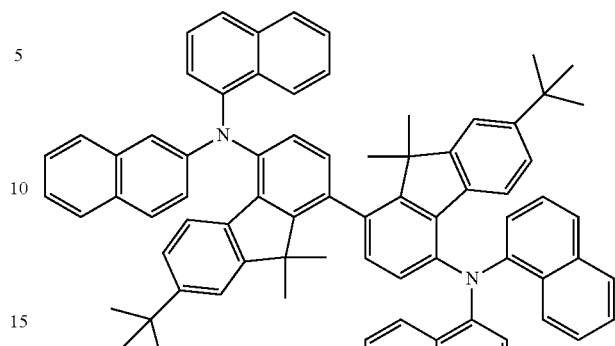
17
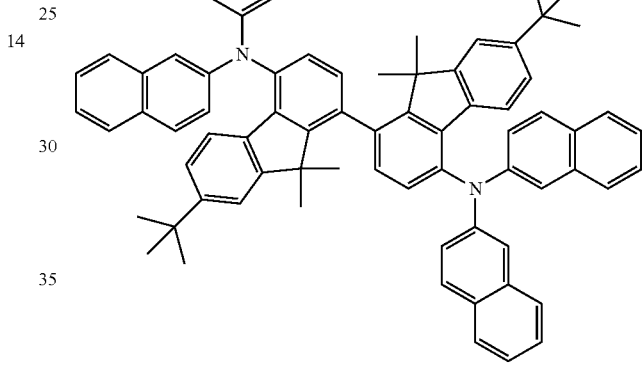
18
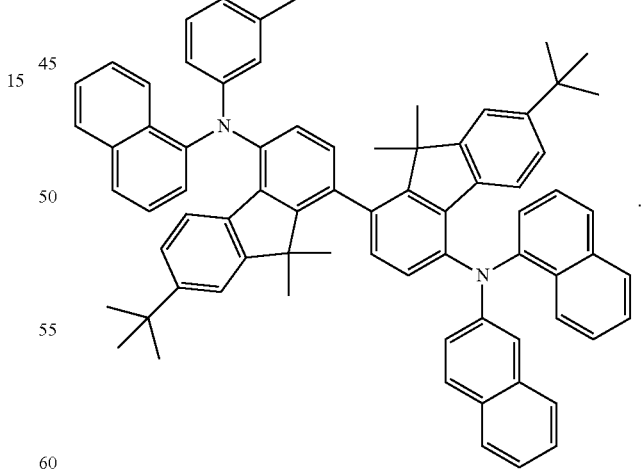
Embodiments are also directed to an organic light emitting diode device including an anode, a cathode, and an organic layer between the anode and the cathode. The organic layer includes the compound represented by Chemical Formula 1.

The organic layer including the compound represented by Chemical Formula 1 may be an electron injection layer (EIL), an electron transport layer (ETL), a hole injection layer (HIL), a hole transport layer (HTL), or an emission layer.

The organic layer including the compound represented by Chemical Formula 1 may be a hole injection layer (HIL) or a hole transport layer (HTL).

Embodiments are also directed to a display device including the organic light emitting diode device including the organic layer that includes the compound represented by Chemical Formula 1.

BRIEF DESCRIPTION OF THE DRAWINGS

Features will become apparent to those of skill in the art by describing in detail exemplary embodiments with reference to the attached drawings in which.

DETAILED DESCRIPTION

Figure 1:
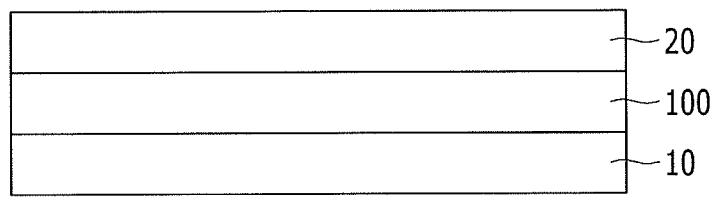
FIGS. 1 to 3 illustrate structures of organic light emitting diode devices according to embodiments.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present. Like reference numerals refer to like elements throughout.

As used herein, when a definition is not otherwise provided, the term "substituted" refers to one substituted with a substituent selected from deuterium, a C1 to C30 alkyl group, a C6 to C30 aryl group, a C2 to C30 heteroaryl group, a C1 to C30 alkoxy group, a C2 to C30 alkenyl group, a C6 to C30 aryloxy group, a C1 to C30 silyloxy group, a C1 to C30 acyl group, a C2 to C30 acyloxy group, a C2 to C30 heteroaryloxy group, C1 to C30 sulfonyl group, a C1 to C30 alkylthiol group, a C6 to C30 arylthiol group, a C1 to C30 heterocyclothiol group, a C1 to C30 phosphoric acid amide group, a C3 to C30 silyl group, NRR' (wherein, R and R' are each independently a substituent selected from a hydrogen atom, a C1 to C30 alkyl group and a C6 to C30 aryl group), a carboxyl group, a halogen, a cyano group, a nitro group, an azo group, a fluorene group, and a hydroxy group.

In addition, two adjacent substituents of the substituted C1 to C30 alkyl group, C6 to C30 aryl group, C2 to C30 heteroaryl group, C1 to C30 alkoxy group, C2 to C30 alkenyl group, C6 to C30 aryloxy group, C1 to C30 silyloxy group, C1 to C30 acyl group, C2 to C30 acyloxy group, C2 to C30 heteroaryloxy group, C1 to C30 sulfonyl group, C1 to C30 alkylthiol group, C6 to C30 arylthiol group, C1 to C30 heterocyclothiol group, C1 to C30 phosphoric acid amide group, C3 to C30 silyl group, NRR' (wherein, R and R' are each independently substituent selected from a hydrogen atom, a C1 to C30 alkyl group and a C6 to C30 aryl group), carboxyl group, halogen, cyano group, nitro group, azo group, fluorene group, or hydroxy group may fused to form a fused ring.

As used herein, the term "unsubstituted" refers to having no substituent.

As used herein, when a definition is not otherwise provided, the term "hetero" refers to 1 to 3 heteroatoms selected from N, O, S, and P, and remaining carbon in one ring.

As used herein, when a definition is not otherwise provided, the term "combination thereof" refers to two or more substituents linked by a linking group, or two or more substituents condensed with each other.

As used herein, the term "organic layer" may refer to a layer including an organic material. It is to be understood that the term "organic layer" may refer to a layer that also includes an inorganic material, a metal complex, or the like, as well as the organic material. The organic layer may include at least one layer.

Representative unsubstituted groups in the Chemical Formulae are defined as follows (carbon numbers of substituents are not limited by the carbon numbers defining the unsubstituted groups).

The unsubstituted C1 to C30 alkyl group may be linear and branched, and, for example, may be methyl, ethyl, propyl, butyl, iso-butyl, tert-butyl, sec-butyl, pentyl, iso-amyl, hexyl, heptyl, octyl, nonyl, dodecyl, or the like.

The unsubstituted C2 to C30 alkenyl group may have at least one carbon double bond in the middle or terminal end of the unsubstituted alkyl group. Examples thereof may include ethenyl, propenyl, butenyl, or the like.

The unsubstituted C2 to C30 alkynyl group may have at least one carbon triple bond in the middle or terminal end of the unsubstituted alkyl group. Examples thereof may include acetylene, propylene, phenylacetylene, naphthylacetylene, isopropylacetylene, t-butylacetylene, diphenylacetylene, or the like.

The unsubstituted C3 to C30 cycloalkyl group may refer to a cyclic alkyl group having 3 to 30 carbon numbers.

The unsubstituted C1 to C30 alkoxy group may refer to —OA (wherein, A is the above-described unsubstituted C1 to C30. Examples thereof include methoxy, ethoxy, propoxy, isopropyloxy, butoxy, pentoxy, or the like.

The term "unsubstituted C6 to C30 aryl group" may refer to a carbocyclic aromatic system having at least one ring. The aryl group may have two or more rings, which may be fused or linked through a single bond and the like. The term "aryl" may include an aromatic system such as phenyl, naphthyl, anthracenyl, and the like. The unsubstituted C6 to C30 aryl group may include, for example, a phenyl group, a biphenyl group, a tolyl group, a naphthyl group, an anthracenyl group, a terphenyl group, a naphthacenyl group, a phenanthrenyl group, a pyrenyl group, a diphenylanthracenyl group, a dinaphthylanthracenyl group, a chrysenyl group, a triphenylenyl group, a perylenyl group, a pentacenyl group, a bromophenyl group, a hydroxyphenyl group, a stilbene group, an azobenzenyl group, or a ferrocenyl group.

The unsubstituted C2 to C30 heteroaryl group may include 1, 2, or 3 heteroatoms selected from N, O, S, and P. The heteroaryl group may have two or more rings, which may be fused or linked through a single bond or the like. Examples of the unsubstituted C2 to C30 heteroaryl group may include a pyrazolyl group, an imidazolyl group, an oxazolyl group, a thiazolyl group, a triazinyl group, a triazolyl group, a tetrazolyl group, an oxadiazolyl group, a thiadiazolyl group, a pyridinyl group, a pyridazinyl group, pyrimidinyl group, a triazinyl group, a carbazolyl group, an indolyl group, a quinolinyl group, an isoquinolinyl group, a thiophene group, a dibenzothiophene group, a dibenzofuran group, or a benzimidazolyl group. Specific examples include substituents [S-1] to [S-25].
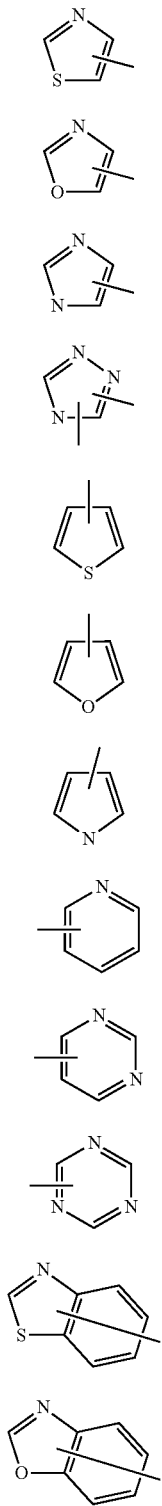
[S-1]
[S-2]
[S-3]
[S-4]
[S-5]
[S-6]
[S-7]
[S-8]
[S-9]
[S-10]
[S-11]
[S-12]
-continued
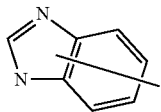
[S-13]
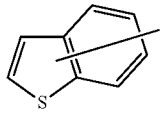
[S-14]
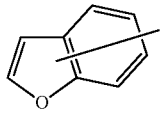
[S-15]
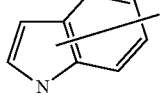
[S-16]
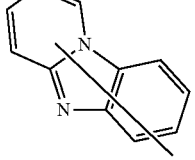
[S-17]
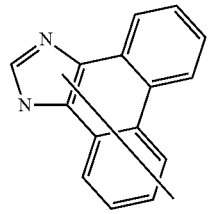
[S-18]
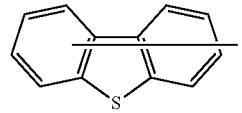
[S-19]
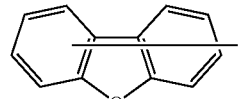
[S-20]
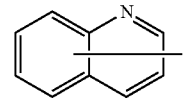
[S-21]
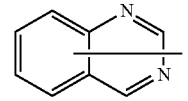
[S-22]
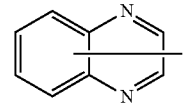
[S-23]

[S-24]

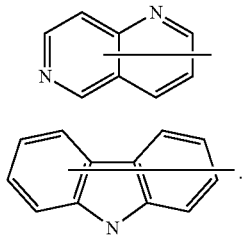

[S-25]

[Chemical Formula 2]

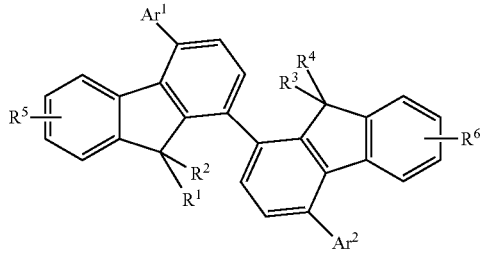

The term "unsubstituted C6 to C30 aryloxy group" may refer to —$OA^1$, wherein $A^1$ is the same functional group as the C6 to C30 aryl group except carbon numbers. Examples of the aryloxy group may include a phenoxy group, or the like.

The term "unsubstituted C6 to C30 arylthio group" may refer to —$SA^1$, wherein $A^1$ is the same functional group as the C6 to C30 aryl group except carbon numbers. Examples of the arylthio group may include a benzenethio group, a naphthylthio group, or the like.

Hereinafter, embodiments are described in detail.

An organic compound according to embodiments is represented by the following Chemical Formula 1:

[Chemical Formula 1]

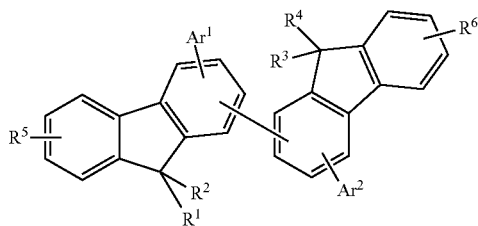

In the above Chemical Formula 1, $R^1$ to $R^6$ are each independently hydrogen, deuterium, a halogen, a substituted or unsubstituted C1 to C30 alkyl group, a substituted or unsubstituted C2 to C30 alkenyl group, a substituted or unsubstituted C2 to C30 alkynyl group, a substituted or unsubstituted C3 to C30 cycloalkyl group, a substituted or unsubstituted C1 to C30 alkoxy group, a substituted or unsubstituted C6 to C30 aryloxy group, a substituted or unsubstituted C6 to C30 arylthiol group, a substituted or unsubstituted C6 to C30 aryl group, a substituted or unsubstituted C2 to C30 heteroaryl group, a substituted or unsubstituted C1 to C30 amine group, a substituted or unsubstituted silyl group, a cyano group, a nitro group, a hydroxy group, a carboxyl group, or a combination thereof, and $Ar^1$ and $Ar^2$ are each independently hydrogen, deuterium, a halogen, a substituted or unsubstituted C1 to C30 alkyl group, a substituted or unsubstituted C6 to C30 aryl group, a substituted or unsubstituted C2 to C30 heteroaryl group, a substituted or unsubstituted C1 to C30 amine group, or a combination thereof.

For example, the compound represented by the above Chemical Formula 1 may be a compound represented by the following Chemical Formula 2.

In the above Chemical Formula 2, $Ar^1$, $Ar^2$, and $R^1$ to $R^6$ are the same as defined in the above Chemical Formula 1.

The compounds represented by the above Chemical Formula 1 or Chemical Formula 2 may have various substituents for substituting the core moiety and thus may have various energy bandgaps.

The compound may have an appropriate energy level depending on the substituents and thus, may fortify hole transport capability or electron transport capability of an organic optoelectronic device and bring about excellent effects with respect to efficiency and driving voltage and also, may have excellent electrochemical and thermal stability and thus, may improve life-span characteristics during the operation of the organic optoelectronic device.

In the specification, the term "hole characteristics" may refer to characteristics that a hole formed in the anode is easily injected into the emission layer and transported in the emission layer due to conductive characteristics according to HOMO level. Specifically, hole characteristics are similar to electron-repelling characteristics.

The term "electron characteristics" may refer to characteristics that an electron formed in the cathode is easily injected into the emission layer and transported in the emission layer due to conductive characteristics according to LUMO level. Specifically, electron characteristics are similar to electron-withdrawing characteristics.

In addition, the compound represented by the above Chemical Formula 1 or Chemical Formula 2 may have a high glass transition temperature (Tg) and thus may have improved thermal stability. Such improved thermal stability may have an important effect on driving stability of an organic light emitting diode device, heat resistance against Joule's heat generated during light emitting of an organic light emitting diode device in an emission layer, between emission layers, or between the emission layer and a metal electrode and high temperature resistance increase, and durability during storage and driving.

In a compound according to one embodiment, $Ar^1$ and $Ar^2$ may be a substituted or unsubstituted C1 to C30 amine group. For example, the compound may have an appropriate energy level as a hole injection and/or a hole transport material by including the amine group. A driving voltage of an organic light emitting diode device may be decreased, and a luminous efficiency may be increased.

An arylamine group is an amine group substituted with an aryl group. The aryl group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted chrysenyl group, a substituted or unsubstituted triphenylenyl group, or a substituted or unsubstituted perylenyl group, as examples.

Ar¹ and Ar² may each independently be a C1 to C30 amine group substituted with a substituted or unsubstituted phenyl group, a substituted or unsubstituted biphenyl group, a substituted or unsubstituted naphthyl group, a substituted or unsubstituted anthracenyl group, or a substituted or unsubstituted phenanthrenyl group, as examples.

Ar¹ and Ar² may be the same. In this case, the compound may have a symmetric structure, and molecular interaction may be improved.

Energy bandgaps may be minutely adjusted by introducing various substituents as well as an arylamine group into the bifluorene structure. Interface characteristics between organic materials may be improved to allow use with various materials.

In one embodiment, the $R^1$ to $R^6$ may each independently be a substituted or unsubstituted C1 to C30 alkyl group, a substituted or unsubstituted C6 to C30 aryl group, or a substituted or unsubstituted C2 to C30 heteroaryl group. For example, the $R^1$ to $R^4$ may be each independently a substituted or unsubstituted C1 to C30 alkyl group.

Specific examples of the compound according to embodiments include the following. The compounds listed in the following Group 1 may be used singularly or as a mixture of at least two, and may be mixed with another compound.

[Group 1]

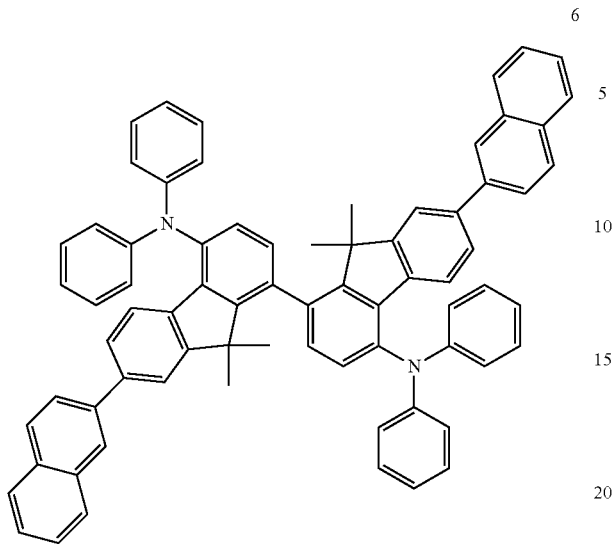
6
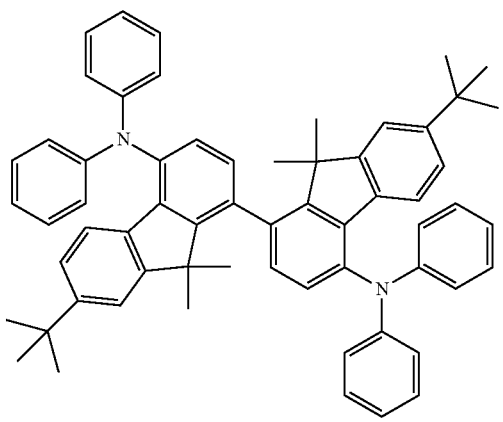
9
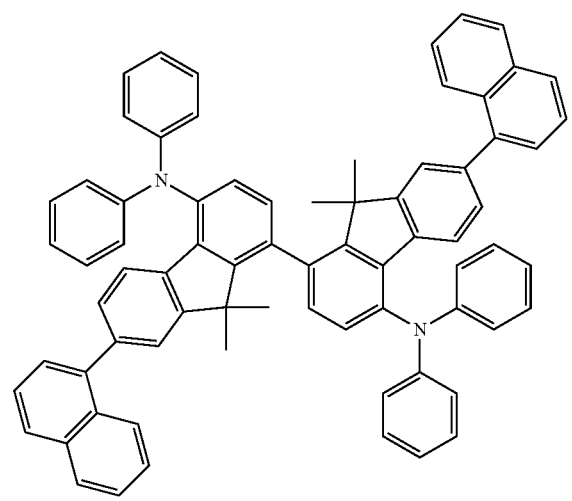
7
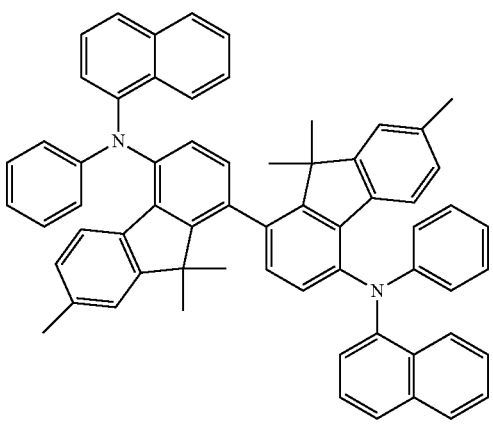
10
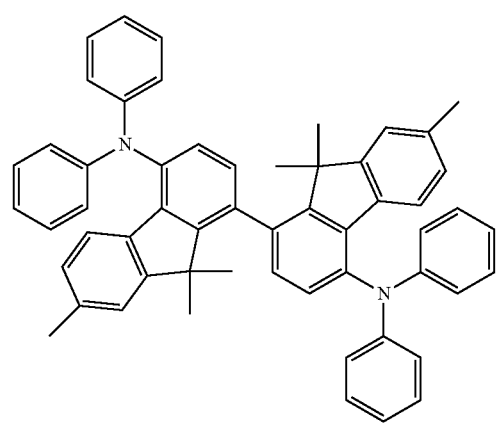
8
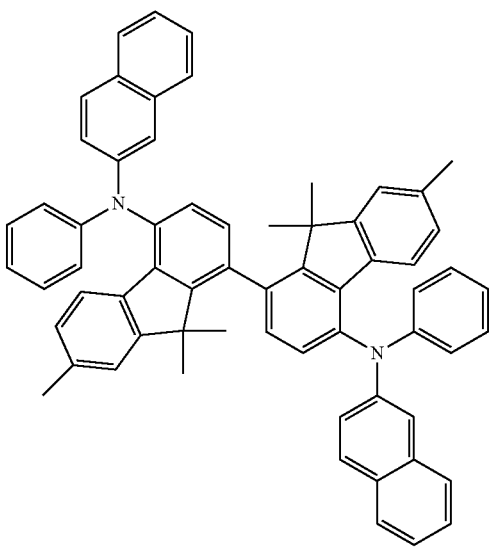
11

12
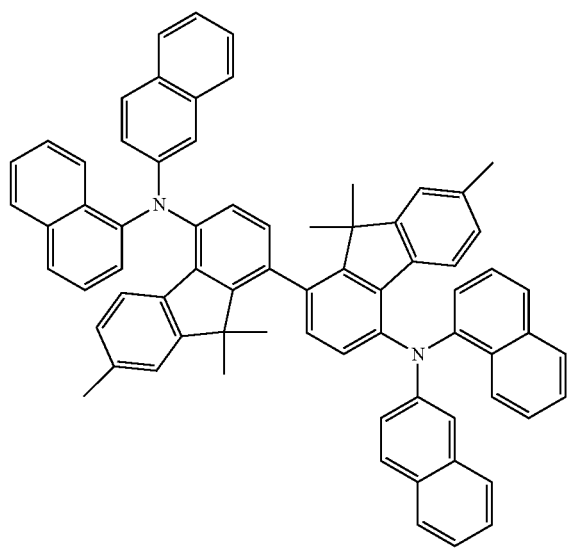
13
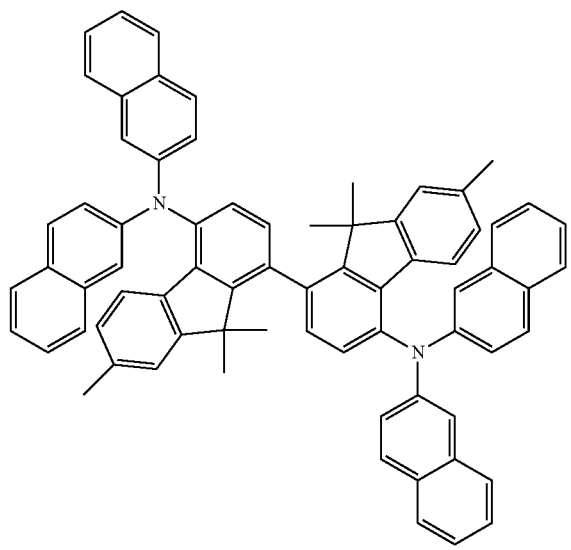
14
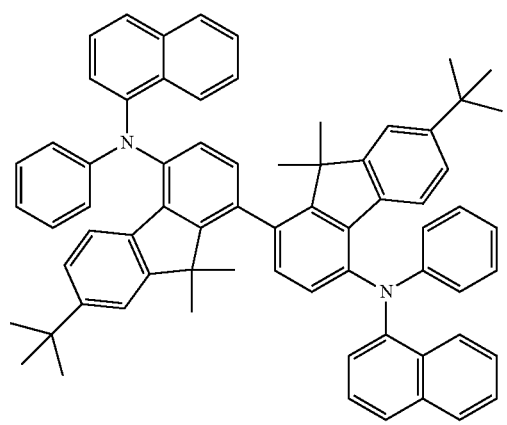
15
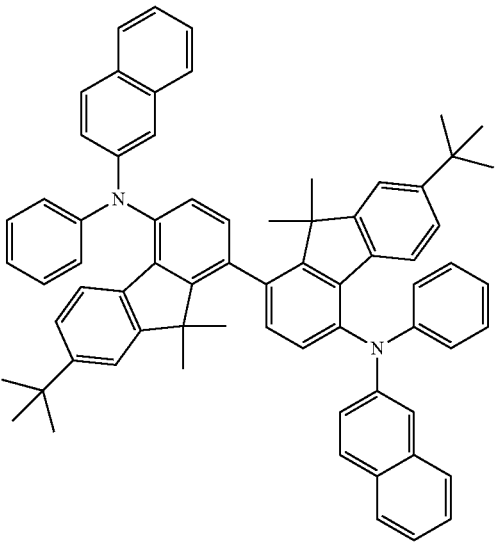
16
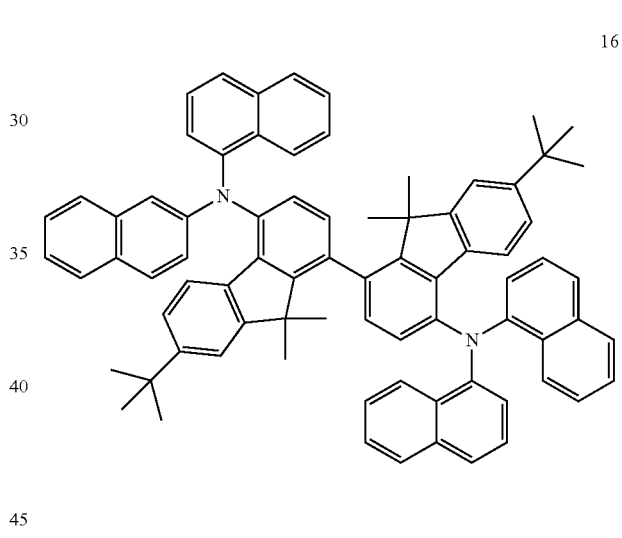
17
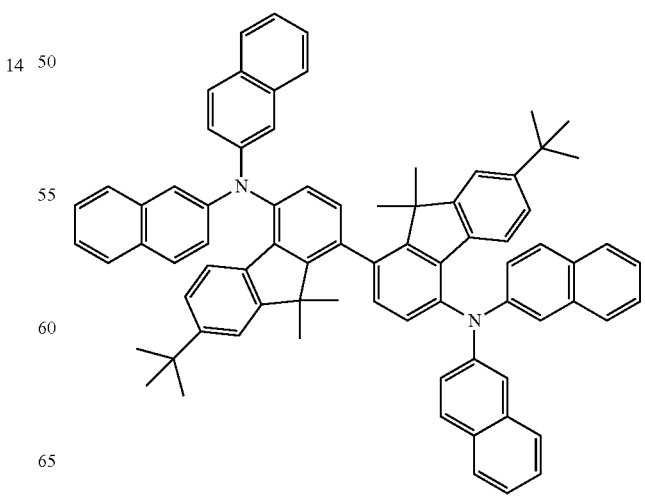

-continued

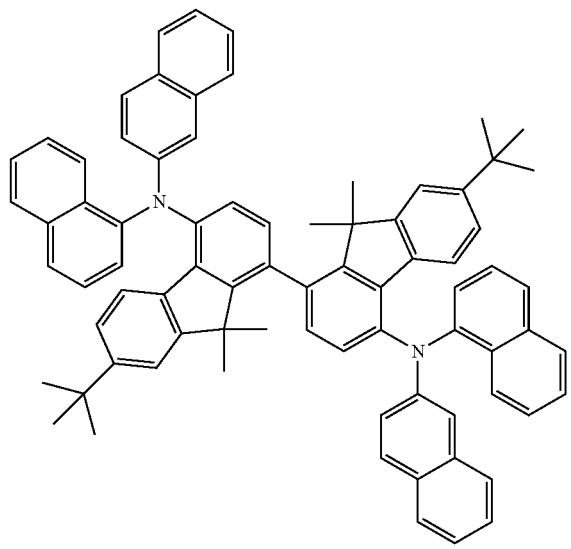

18

The compounds listed in the Group 1 are referred to be compounds 1 to 18 (The numbers under compounds denotes the number of each compound).

Hereinafter, an organic light emitting diode device according to one embodiment including the organic compound is described referring to FIGS. 1 to 3.

Figure 2:
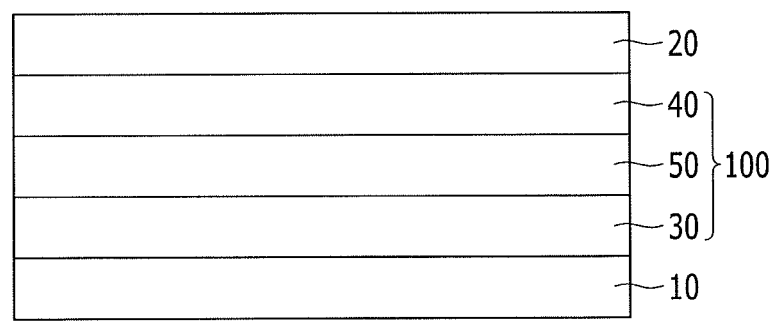
Figure 3:
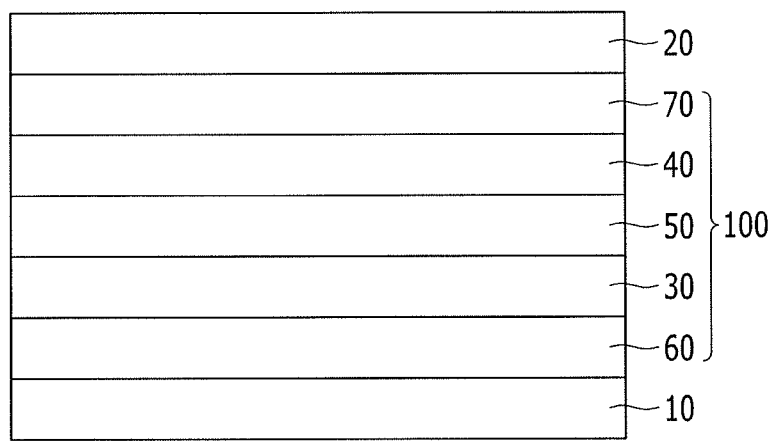

FIGS. 1 to 3 illustrate cross-sectional views of organic light emitting diode devices according to an embodiment.

Referring to FIG. 1, an organic light emitting diode device according to an embodiment includes an anode 10, a cathode 20 facing the anode 10, and an organic layer 100 interposed between the anode 10 and the cathode 20.

The organic layer 100 includes the compound represented by Chemical Formula 1 described above.

The organic layer 100 may be formed by various methods such as, for example, vacuum deposition, a spin coating, a casting, LB, or the like.

When the organic layer is formed by the vacuum deposition, the deposition conditions may differ according to the compound used as the material for the organic layer, the structure of the desired organic layer, and thermal characteristics. Generally, the deposition conditions may be appropriately selected within the ranges of a deposition temperature of about 100 to about 500° C., a vacuum degree of about $10^{-8}$ to about $10^{-3}$ torr, and a deposition rate of about 0.01 to about 100 Å/sec, as examples.

When the organic layer is formed by the spin coating, the coating conditions may differ according to the compound used as a material for the organic layer, the structure of the desired organic layer, and thermal characteristics or the like. For example, the coating conditions may be suitably selected from the ranges of a coating speed of about 2,000 rpm to about 5,000 rpm, and a heat treatment temperature of about 80° C. to about 200° C. for removing the solvent after coating.

The substrate (not shown) may be disposed on the side of anode 10 or on the side of cathode 20. The substrate may be made of an inorganic material such as glass or an organic material such as polycarbonate, polymethylmethacrylate, polyethyleneterephthalate, polyethylenenaphthalate, polyamide, polyethersulfone, or a combination thereof, silicon wafer, or the like.

The anode 10 may be a transparent electrode or an opaque electrode. The transparent electrode may be formed of, for example, a conductive oxide such as indium tin oxide (ITO), indium zinc oxide (IZO), tin oxide ($SnO_2$), zinc oxide (ZnO), or a combination thereof, or a metal such as aluminum silver, or magnesium, in a thin thickness. The opaque electrode may be made of, for example, a metal such as aluminum, silver, or magnesium.

The cathode 20 may include a material having a small work function, such that electrons may be easily injected thereinto. For example, the material having a small work function may include a metal such as magnesium, calcium, sodium, potassium, titanium, indium, yttrium, lithium, gadolinium, aluminum silver, tin, lead, cesium, barium, or the like, or an alloy thereof, or a multi-layer structure material such as LiF/Al, $LiO_2$/Al, LiF/Ca, LiF/Al, and $BaF_2$/Ca, or the like. The cathode may be a metal electrode such as aluminum or the like.

Hereinafter, an organic light emitting diode device according to another embodiment is illustrated referring to FIG. 2.

Referring to FIG. 2, an organic light emitting diode device according to this embodiment includes the anode 10 and the cathode 20, and an organic layer 100 interposed between the anode 10 and the cathode 20, like the above embodiment. The organic layer 100 further includes an emission layer 50 interposed between the anode 10 and the cathode 20, a hole transport layer (HTL) 30 interposed between the anode 10 and the emission layer 50, and an electron transport layer (ETL) 40 interposed between the cathode 20 and the emission layer 50.

The hole transport layer (HTL) 30 may include the compound represented by Chemical Formula 1. Accordingly, hole mobility may be increased.

The hole transport layer (HTL) 30 may further include a p-dopant in order to improve film conductivity.

Examples of the p-dopant include a quinone derivative such as tetracyanoquinone dimethane (TCNQ) and 2,3,5,6-tetrafluoro-tetracyano-1,4-benzoquinone dimethane (F4-CTNQ), or the like, metal oxides such as tungsten oxide and molybdenum oxide, or a cyano group-containing compound such as the following compound 100.

[Compound 100]

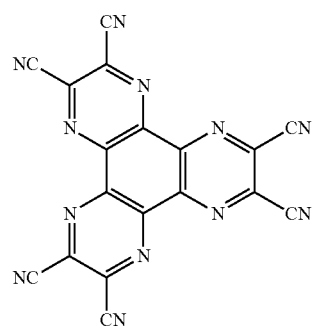

When the hole transport layer (HTL) 30 further includes the p-dopant, the p-dopant may be uniformly or non-uniformly dispersed among the layers, which provides various modifications.

The emission layer 50 may include only a single compound, or a mixture of an organic compound and another organic compound. In the mixture, a larger amount of one compound may function as a fluorescent or phosphorescent host, and a lesser amount of another compound may function as a dopant.

Examples of a host include Alq3, 4,4'-N,N'-dicarbazole-biphenyl (CBP), polyvinylcarbazole (PVK), 9,10-di(naphthalen-2-yl)anthracene (ADN), 4,4',4''-tris(carbazol-9-yl)-triphenylamine (TCTA), 1,3,5-tris(N-phenylbenzimidazol-2-yl)benzene (TPBI), 3-tert-butyl-9,10-di(naphth-2-yl)anthracene (TBADN), E3, distyrylarylene (DSA), or the like.

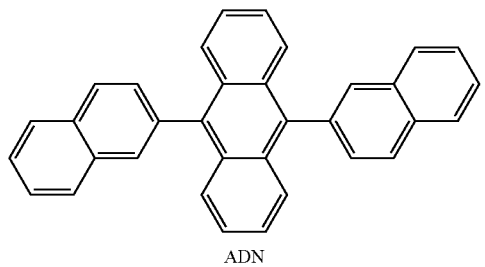 [SMILES: c1ccc2cc(-c3c4ccccc4c(-c4ccc5ccccc5c4)c4ccccc34)ccc2c1]

ADN

Examples of red dopants include PtOEP, Ir(piq)$_3$, Btp$_2$Ir(acac), DCJTB, or the like.

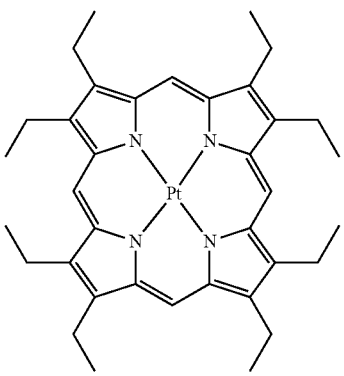

PtOEP

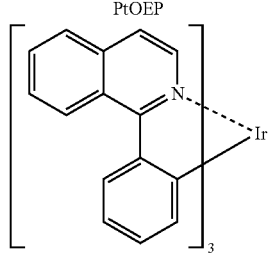

Ir(piq)$_3$

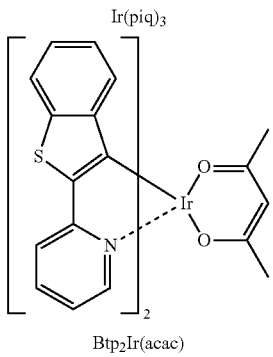

Btp$_2$Ir(acac)

Examples of green dopants include Ir(ppy)$_3$ (ppy=phenylpyridine), Ir(ppy)$_2$(acac), Ir(mpyp)$_3$, C545T, or the like.

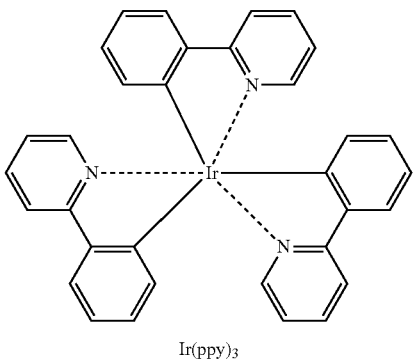

Ir(ppy)$_3$

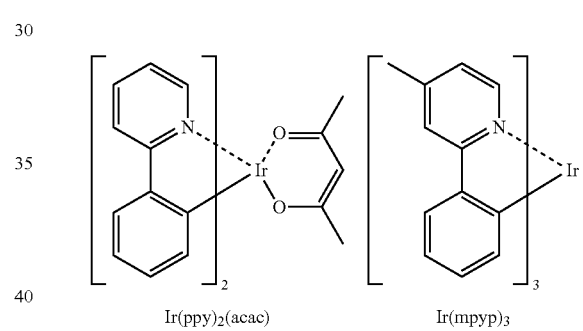

Ir(ppy)$_2$(acac)    Ir(mpyp)$_3$

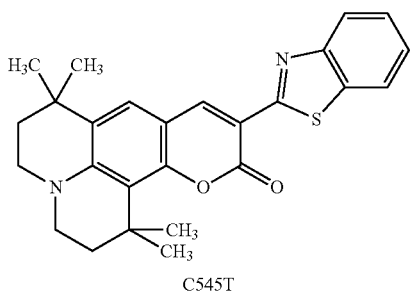

C545T

Examples of blue dopants include F$_2$Irpic, (F$_2$ppy)$_2$Ir(tmd), Ir(dfppz)$_3$, ter-fluorene, 4,4'-bis(4-diphenylaminostyryl)biphenyl (DPAVBi), 2,5,8,11-tetra-ter-butyl perylene (TBP), or the like.

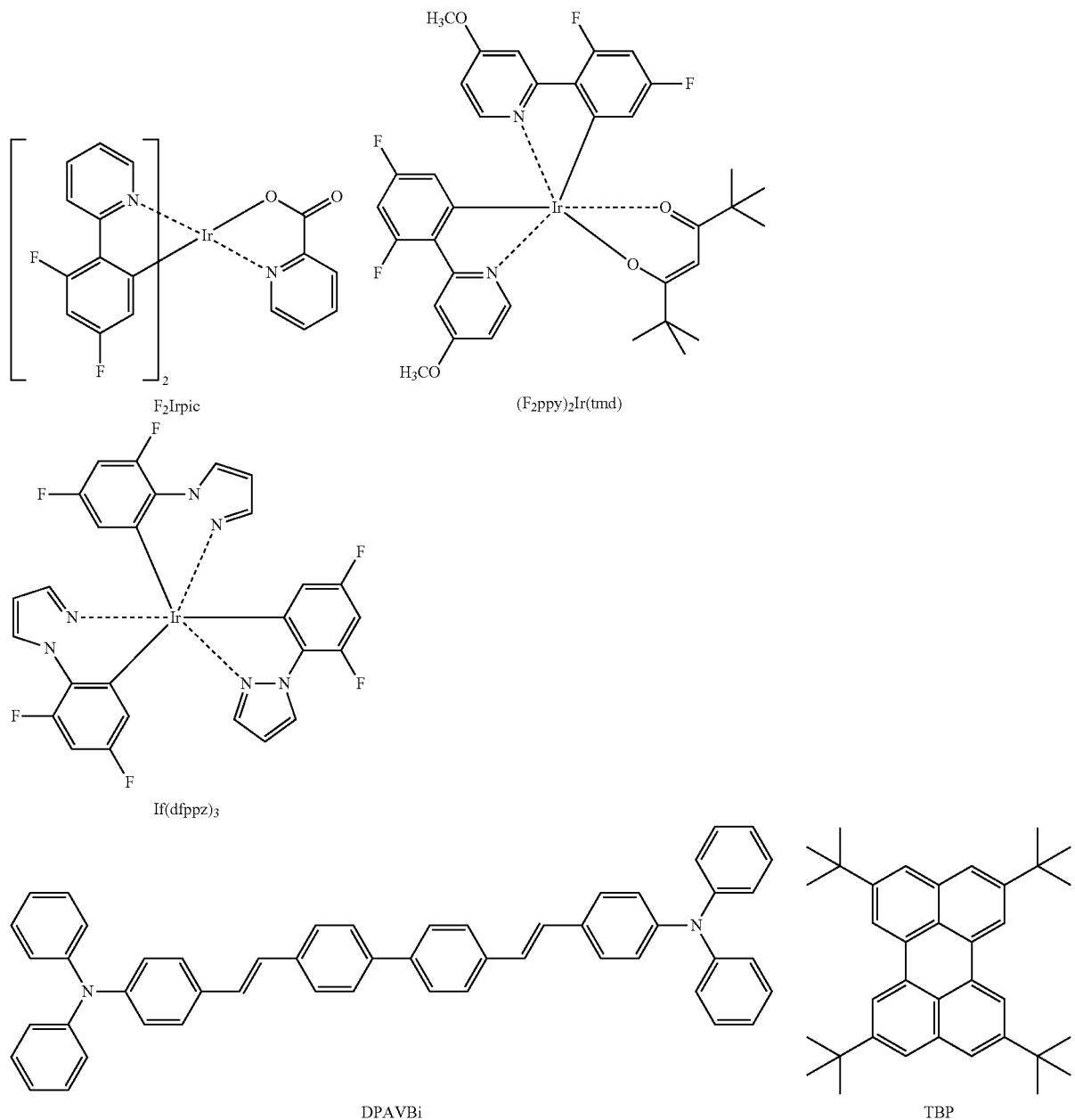

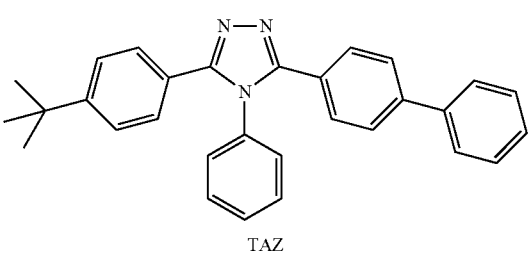

A content of the dopant may be about 0.1 to about 15 parts by weight based on the total weight, 100 parts by weight of an emission layer-forming material (i.e., a total weight of the host and dopant is 100 parts by weight), as an example. Within the above range of the dopant, a concentration extinction phenomenon may be substantially suppressed.

The emission layer 50 may emit white light by a combination of three primary colors—red, green, and blue. The combination of colors may be provided by a combination of adjacent sub-pixels to emit white light or by a stack in a vertical direction to emit white light.

The electron transport layer (ETL) may include a suitable electron transport layer (ETL)-forming material. For example, a material such as a quinoline derivative, particularly tris(8-quinolinolate)aluminum $Alq_3$, TAZ, Balq, or the like may be used.

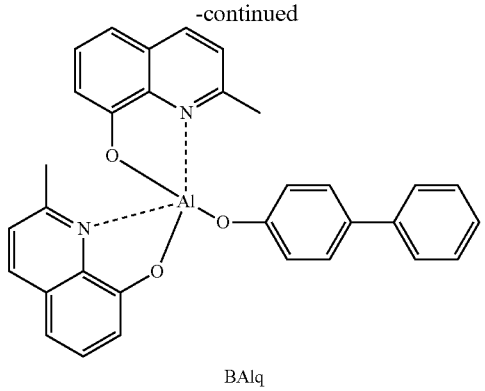

BAlq

An electron transport layer (ETL) of an organic light emitting diode device according to one embodiment may include an electron transport organic compound and a metal-containing material. Examples of the electron transport organic compound include an anthracene-based compound such as 9,10-di(naphthalen-2-yl)anthracene (ADN), the following compound 101, or the following compound 102, or the like.

[Compound 101]

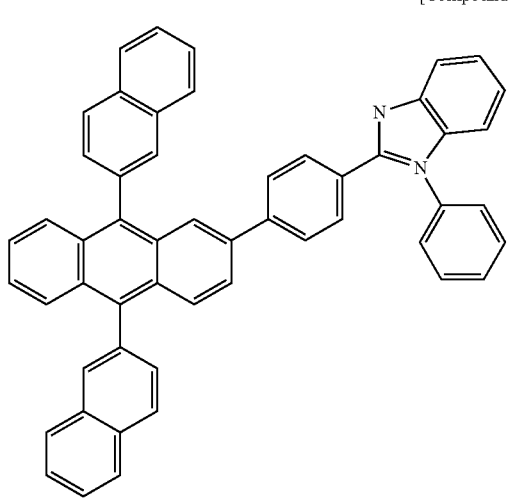

[Compound 102]

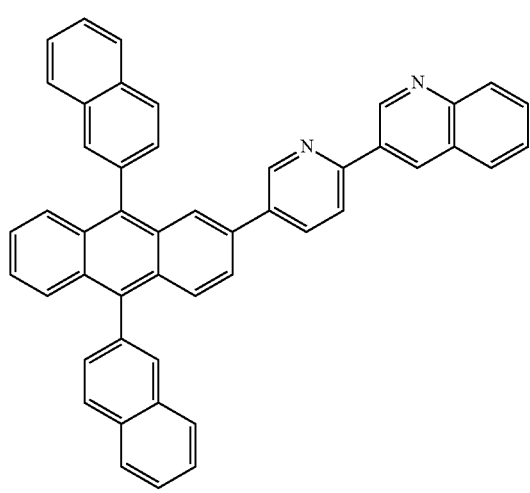

The metal-containing material may include a Li complex. Examples of the Li complex include lithium quinolate (LiQ) or the following compound 103.

[Compound 103]

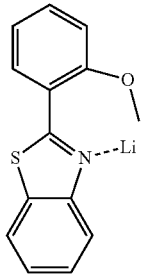

Hereinafter, referring to FIG. 3, an organic light emitting diode device according to another embodiment is described.

Referring to FIG. 3, an organic light emitting diode device according to this embodiment includes an anode 10 and a cathode 20 facing each other, an emission layer 50 interposed between the anode 10 and the cathode 20, a hole transport layer (HTL) 30 interposed between the anode 10 and the emission layer 50, and an electron transport layer (ETL) 40 interposed between the cathode 20 and the emission layer 50, like the above embodiment.

The organic light emitting diode device according to the present embodiment further includes a hole injection layer (HIL) 60 interposed between the anode 10 and the hole transport layer (HTL) 30 and an electron injection layer (EIL) 70 interposed between the cathode 20 and the electron transport layer (ETL) 40.

The hole injection layer (HIL) 60 may include a suitable hole injection material, for example, a phthalocyanine compound such as copper phthalocyanine, or the like, m-MTDATA [4,4',4"-tris(3-methylphenylphenylamino)triphenylamine], NPB (N,N'-di(1-naphthyl)-N,N'-diphenylbenzidine), TDATA, 2T-NATA, Pani/DBSA (polyaniline/dodecylbenzene sulfonic acid), PEDOT/PSS (poly(3,4-ethylenedioxythiophene)/poly(4-styrenesulfonate), Pani/CSA (polyaniline/camphor sulfonic acid) or PANI/PSS (polyaniline)/poly(4-styrenesulfonate)), or the like.

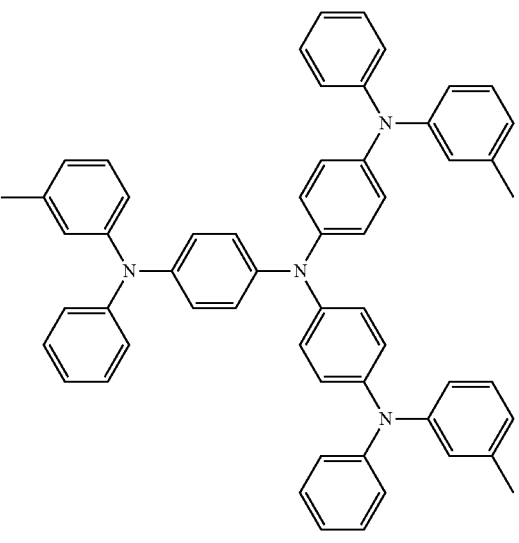

m-MTDATA

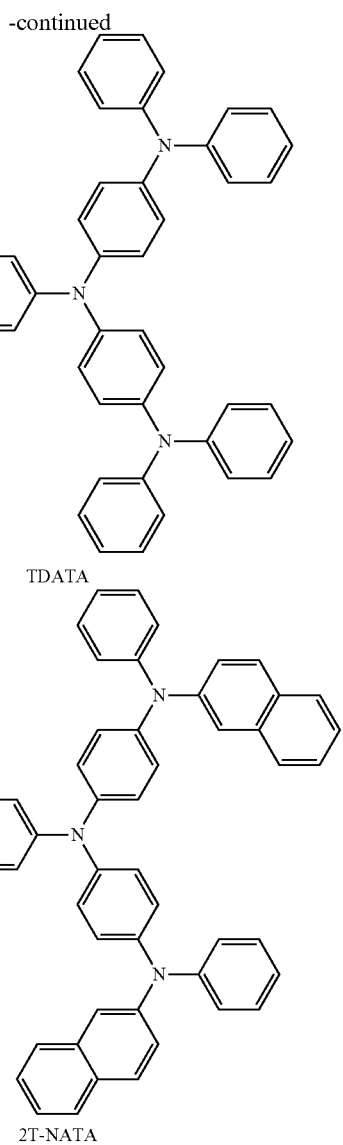

TDATA

2T-NATA

The hole injection layer (HIL) 60 may further include the above p-dopant in order to improve film conductivity.

When the hole injection layer (HIL) 60 further includes a p-dopant, the p-dopant may be uniformly or non-uniformly dispersed among the layers. Thus, various modifications may be provided.

The hole injection layer (HIL) 60 may be formed on the anode 10 using various methods such as a vacuum deposition method, a spin coating method, a cast method, or an LB method.

When the hole injection layer (HIL) 60 is formed by vacuum deposition, the deposition conditions may be differ according to the particular compound used as the material for the hole injection layer (HIL) 60, the structure of the objective hole injection layer (HIL), and the thermal characteristics. For example, deposition conditions may be appropriately selected within the ranges of a deposition temperature of about 100 to about 500° C., a vacuum degree of about $10^{-8}$ to about $10^{-3}$ torr, and a deposition rate of about 0.01 to about 100 Å/sec.

When the hole injection layer (HIL) 60 is formed by the spin coating, the coating conditions may differ according to the particular compound used as a material for the hole injection layer (HIL), the structure of the objective hole injection layer (HIL), and the thermal characteristics or the like. For example, coating conditions may be suitably selected from the ranges of a coating speed of about 2,000 rpm to about 5,000 rpm, and a heat treatment temperature of about 80° C. to about 200° C. for removing the solvent after coating.

When the emission layer 50 includes a phosphorescent dopant, a hole blocking layer (not shown) may be formed on the emission layer 50 to prevent the phenomenon that a triplet exciton or hole diffuses into the electron transport layer (ETL). The hole blocking layer material i may be selected from suitable hole blocking layer materials, such as an oxadiazole derivative or a triazole derivative, phenanthroline derivative, Balq, BCP or the like.

In addition, an electron injection layer (EIL) 70 may be stacked on the electron transport layer (ETL) 40 as a material having functions of easily injecting electrons from the cathode.

The electron injection layer (EIL) 70 may include a suitable material for forming an electron injection layer (EIL), such as LiF, NaCl, CsF, $Li_2O$, BaO, or the like. The deposition conditions or the coating conditions of the electron injection layer (EIL) 70 may differ according to the compound used. For example, the deposition conditions or coating conditions may be similar to the condition ranges for forming the hole injection layer (HIL) 60.

The organic light emitting diode device according to implementations may have a structure of an anode/hole injection layer (HIL)/emission layer/cathode, anode/hole injection layer (HIL)/hole transport layer (HTL)/emission layer/electron transport layer (ETL)/cathode, or a structure of an anode/hole injection layer (HIL)/hole transport layer (HTL)/emission layer/electron transport layer (ETL)/electron injection layer (EIL)/cathode structure. In other implementations, the organic light emitting diode device may have a structure of an anode/functional layer simultaneously having hole injection function and hole transport function/emission layer/electron transport layer (ETL)/cathode or a structure of an anode/functional layer simultaneously having a hole injection function and a hole transport function/emission layer/electron transport layer (ETL)/electron injection layer (EIL)/cathode. In other implementations, the organic light emitting diode device may have a structure of an anode/hole transport layer (HTL)/emission layer/functional layer simultaneously having electron injection function and electron transport function/cathode, anode/hole injection layer (HIL)/emission layer/functional layer simultaneously having electron injection function and electron transport function/cathode, or a structure of an anode/hole injection layer (HIL)/hole transport layer (HTL)/emission layer/functional layer simultaneously having electron injection function and electron transport function/cathode structure, as examples.

The organic light emitting diode device may be, for example, electrically connected to a thin film transistor. The thin film transistor may be disposed between the substrate and the electrode.

Another embodiment may provide a display device including the organic light emitting diode device according to above one embodiment.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

SYNTHESIS EXAMPLES

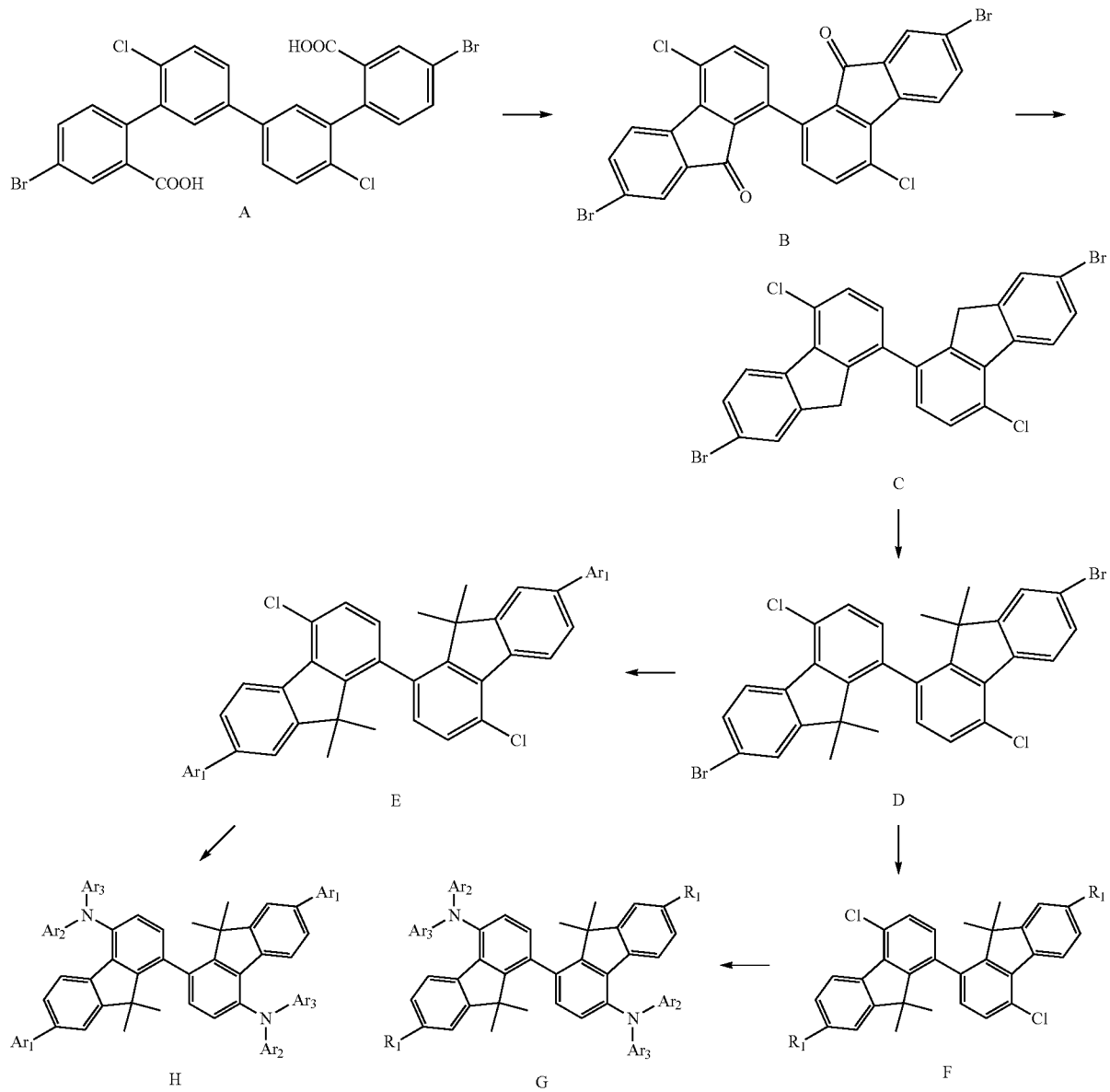

Synthesis of Intermediate B 120 ml of strong sulfuric acid was put into a 250 ml triangle flask, and 2.90 g (9.11 mmol) of a compound A was slowly added thereto to prepare a mixture. The mixture was agitated for 2 hours at 25° C., and ice was added to the flask. A purple precipitate produced therein was filtered and rinsed with distilled water. The obtained purple solid was added to a potassium carbonate solution, and the mixture was agitated for a moment, filtered, washed with distilled water, and dried in a oven at 110° C., obtaining 2.39 g (8.45 mmol, 92.9%) of an intermediate B.

$^1$H NMR (500 MHz, THF D8), d (ppm): 7.93 (2H, d), 7.68-7.57 (4H, m), 7.48-7.42 (4H, m), HRMS for $C_{26}H_{10}Br_2Cl_2O_2$ [M]+: calculation value 585.07, measurement value 584

Synthesis of Intermediate C 3.47 g (61.9 mmol) of potassium hydroxide and 30 ml of diethylene glycol were put into a 500 ml round-bottomed flask and agitated. 7 g (2.479 mmol) of the intermediate B and 2.54 g (50.8 mmol) of hydrazine monohydrate were added to the flask, and the mixture was agitated at 180° C. to 190° C. for 24 hours. When the reaction was complete, the resultant was cooled with ice and acidificated. Hydrochloric acid was put in a 500 ml beaker, the resultant mixture was added thereto, and the obtained mixture was agitated. The produced white precipitate was filtered, dried, and recrystallized by acetic acid, obtaining 4.3 g (1.23 mmol) of an intermediate C (a yield=49.7%).

¹H NMR (500 MHz, THF D8), d (ppm): 8.108 (s, 2H); 7.941 (d, 2H); 7.600 (d J=6.9, 2H); 7.399 (t J=6.9, 2H); 7.312 (t J=6.9, 2H); 3.997 (s, 4H)

HRMS for $C_{26}H_{14}Br_2Cl_2$ [M]+: calculation value: 557.1, measurement value: 556

Synthesis of Intermediate D 30 g (0.18 mol) of the intermediate C was put into a 2000 ml round-bottomed flask and vacuum-dried, and then, the flask was filled with argon gas. 18 ml of THF was put into the flask, and the flask was cooled down to −78° C. 16.2 ml (0.259 mol) of n-butyl lithium (1.6M in Hex.) was slowly added to the flask, and the mixture was agitated for one hour. After the resultant was cooled down to −78° C. again, 5.46 g (0.283 mol) of 1-bromomethyl was added to the resultant, and the resulting mixture was agitated for 1 hour. After being cooled down to −78° C. again, 16.2 ml (0.259 mol) of n-butyl lithium (1.6M in Hex.) was slowly added to the resultant, and the resulting mixture was agitated for 1 hour. After being cooled down to −78° C. a final time, 5.46 g (0.283 mol) of 1-bromomethyl was added thereto, and the resulting mixture was agitated for one hour. When the reaction was complete, the reactant was rinsed with distilled water and extracted with petroleum ether, and an extract was filtered and dried after removing moisture therefrom with magnesium sulfate. The obtained material was purified through column chromatography (Eluent=Petroleum ether) and recrystallized with ethanol, obtaining 5.47 g (0.778 mol) of a compound D (a yield=65.9%).

¹H NMR (500 MHz, THF D8), d (ppm): 7.72 (2H, d), 7.72-7.55 (4H, m), 7.45-7.42 (4H, m), 1.67-1.65 (12H, t)

HRMS for $C_{30}H_{22}Br_2Cl_2$ [M]+: calculation value 613.21, measurement value 612

Synthesis of Intermediate E 30 g (0.572 mol) of the intermediate D, (1.144 mol) of $Ar_1-B(OH)_2$, and 0.03 eq of tetrakis(triphenylphosphine) palladium were put in a 3000 ml round-bottomed flask and vacuum-dried, and the flask was filled with nitrogen gas. Toluene was added to the flask to dissolve the compounds, 5.72 mol of a 2.0M potassium carbonate aqueous solution and 52.7 mmol of Aliquat 336 were added thereto, and the mixture was refluxed and agitated at 120° C. for 2 hours. When the reaction was complete, the resultant was extracted with MC and purified through column chromatography (Eluent=MC:Hex), obtaining an intermediate E (a yield=45.9%).

($Ar_1$=a phenyl group)

¹H NMR (500 MHz, THF D8), d (ppm): 7.72 (2H, d), 7.72-7.55 (8H, m), 7.45-7.42 (10H, m), 1.67-1.65 (12H, t)

HRMS for $C_{42}H_{32}Cl_2$ [M]+: calculation value 607.61, measurement value 606

($Ar_1$=a naphthyl group)

¹H NMR (500 MHz, THF D8), d (ppm): 8.11-8.01 (4H, m), 7.72 (2H, d), 7.72-7.55 (8H, m), 7.45-7.42 (10H, m), 1.67-1.65 (12H, t)

HRMS for $C_{50}H_{36}Cl_2$ [M]+: calculation value 707.73, measurement value 706

Synthesis of Intermediate F 10 g (0.016 mol) of the intermediate F was put in a 2000 ml round-bottomed flask and vacuum-dried, and the flask was filled with argon gas. 18 ml of THF was added to the flask, and the mixture was cooled down to −78° C. 25.8 ml (0.04 mol) of n-butyl lithium (1.6M in Hex.) was slowly added thereto, and the mixture was agitated for 1 hour. The resultant was cooled down to −78° C., 0.035 mol of $R_1-Br$ was added thereto, and the mixture was agitated for one hour. When the reaction was complete, the resultant was washed with distilled water and extracted with MC. The produced extract was filtered and dried after removing moisture with magnesium sulfate. The obtained material was purified through column chromatography (MC:Hex), obtaining an intermediate F (a yield=75%).

($R_1$=a methyl group)

¹H NMR (500 MHz, THF D8), d (ppm): 7.72 (2H, d), 7.72-7.55 (8H, m), 7.45-7.42 (10H, m), 1.67-1.65 (18H, t)

HRMS for $C_{32}H_{28}Cl_2$ [M]+: calculation value 483.47, measurement value 482

($R_1$=a t-butyl group)

¹H NMR (500 MHz, THF D8), d (ppm): 8.11-8.01 (4H, m), 7.72 (2H, d), 7.72-7.55 (8H, m), 7.45-7.42 (10H, m), 1.67-1.65 (30H, m)

HRMS for $C_{38}H_{40}Cl_2$ [M]+: calculation value 567.63, measurement value 566

Synthesis Example 1

Synthesis of Compound 1

10 g (0.016 mol) of the synthesized intermediate E, 6.09 g (0.036 mol) of diphenylamine, 16.0 mg (17.4 μmol) of tris(dibenzylidineacetone)dipalladium, 1.4 g (0.072 mmol) of sodium tert-butoxide, and 100.4 mg (34.8 mop of (2-biphenyl)di-tert-butylphosphine were put in a flask and vacuum-dried, and the flask was filled with argon gas. 250 ml of toluene was added to the flask to dissolve the compounds therein, and the solution was refluxed and agitated for 12 hours at 120° C. When the reaction was complete, a solid obtained by adding methanol in an excessive amount to the reaction flask, filtered, dissolved in dichloro-methane, washed with distilled water, extracted, and dried. The obtained material was recrystallized by acetonitrile, obtaining 10.3 g of Compound 1 (a yield=74.1%).

¹H NMR (500 MHz, THF D8), d (ppm): 7.72 (2H, d), 7.72-7.55 (8H, m), 7.45-7.42 (16H, m), 7.01-6.46 (4H, m), 1.67-1.65 (12H, t)

HRMS for $C_{66}H_{52}N_2$ [M]+: calculation value 873.13, measurement value 872

Synthesis Example 2

Synthesis of Compound 4

Compound 4 was obtained according to the same method as Synthesis Example 1 except for using N-(naphthalen-2-yl)naphthalen-1-amine instead of diphenylamine (a yield=71.4%).

¹H NMR (500 MHz, THF D8), d (ppm): 7.80-7.72 (4H, m), 7.72-7.55 (20H, m), 7.45-7.42 (20H, m), 7.01-6.46 (4H, m), 1.67-1.65 (12H, t)

HRMS for $C_{82}H_{60}N_2$ [M]+: calculation value 1073.37, measurement value 1072

Synthesis Example 3

Synthesis of Compound 5

Compound 5 was obtained according to the same method as Synthesis Example 1 except for using N-(naphthalen-1-yl)naphthalen-1-amine instead of diphenylamine (a yield=72.9%).

¹H NMR (500 MHz, THF D8), d (ppm): 7.80-7.72 (4H, m), 7.72-7.55 (19H, m), 7.45-7.42 (21H, m), 7.01-6.46 (4H, m), 1.67-1.65 (12H, t)

HRMS for $C_{82}H_{60}N_2$ [M]+: calculation value 1073.37, measurement value 1072

Synthesis Example 4

Synthesis of Compound 6

Compound 6 was prepared according to the same method as Synthesis Example 1 except for using N-(naphthalen-1-yl)naphthalen-1-amine instead of diphenylamine (a yield=69.2%).
$^1$H NMR (500 MHz, THF D8), d (ppm): 7.80-7.72 (4H, m), 7.72-7.55 (22H, m), 7.45-7.42 (20H, m), 7.01-6.46 (2H, m), 1.67-1.65 (12H, t)
HRMS for $C_{90}H_{64}N_2$ [M]+: calculation value 1173.18, measurement value 1172

Synthesis Example 5

Synthesis of Compound 10

Compound 10 was prepared according to the same method as Synthesis Example 1 except for using the intermediate F instead of the intermediate E (a yield=76%).
$^1$H NMR (500 MHz, THF D8), d (ppm): 7.72 (4H, m), 7.72-7.55 (16H, m), 7.45-7.42 (14H, m), 1.67-1.65 (18H, t)
HRMS for $C_{64}H_{52}N_2$ [M]+: calculation value 849.11, measurement value 848

Synthesis Example 6

Synthesis of Compound 18

Compound 10 was prepared according to the same method as Synthesis Example 1 except for using the intermediate F instead of the intermediate E and N-(naphthalen-2-yl)naphthalen-1-amine instead of diphenylamine (a yield=71.4%).
$^1$H NMR (500 MHz, THF D8), d (ppm): 8.11-8.01 (4H, m), 7.72 (4H, m), 7.72-7.55 (16H, m), 7.45-7.42 (14H, m), 1.67-1.65 (30H, m)
HRMS for $C_{78}H_{68}N_2$ [M]+: calculation value 1033.39, measurement value 1032

EXAMPLES

Example 1

An anode was manufactured by cutting a 15 Ω/cm² (500 Å) ITO glass substrate (Corning Inc.) into a size of 50 mm×50 mm×0.5 mm, washing the glass substrate with isopropyl alcohol and pure water respectively for 10 minutes, radiating ultraviolet (UV) for 10 minutes, and mounting the resultant in a vacuum deposition device. A 600 Å-thick hole injection layer (HIL) was formed on the substrate by vacuum depositing 2-TNATA, and subsequently, a 300 Å-thick hole transport layer (HTL) was formed thereto by vacuum-depositing Compound 1.

On the hole transport layer (HTL), a 300 Å-thick emission layer was formed by simultaneously depositing ADN as a host material and N1,N1'-(biphenyl-4,4'-diyl)bis(N1-phenyl-N4,N4-di-m-tolylbenzene-1,4-diamine (hereinafter, DNPTD) (a doping amount of 5%) as a blue dopant material. Subsequently, a 300 Å-thick electron transport layer (ETL) was formed on the emission layer by depositing Alq3, and a 1,200 Å-thick Al electrode was formed thereon by vacuum depositing Al as a cathode, manufacturing an organic light emitting diode device. The structure of the organic light emitting diode device according to Example 1 is summarized in Table 1.

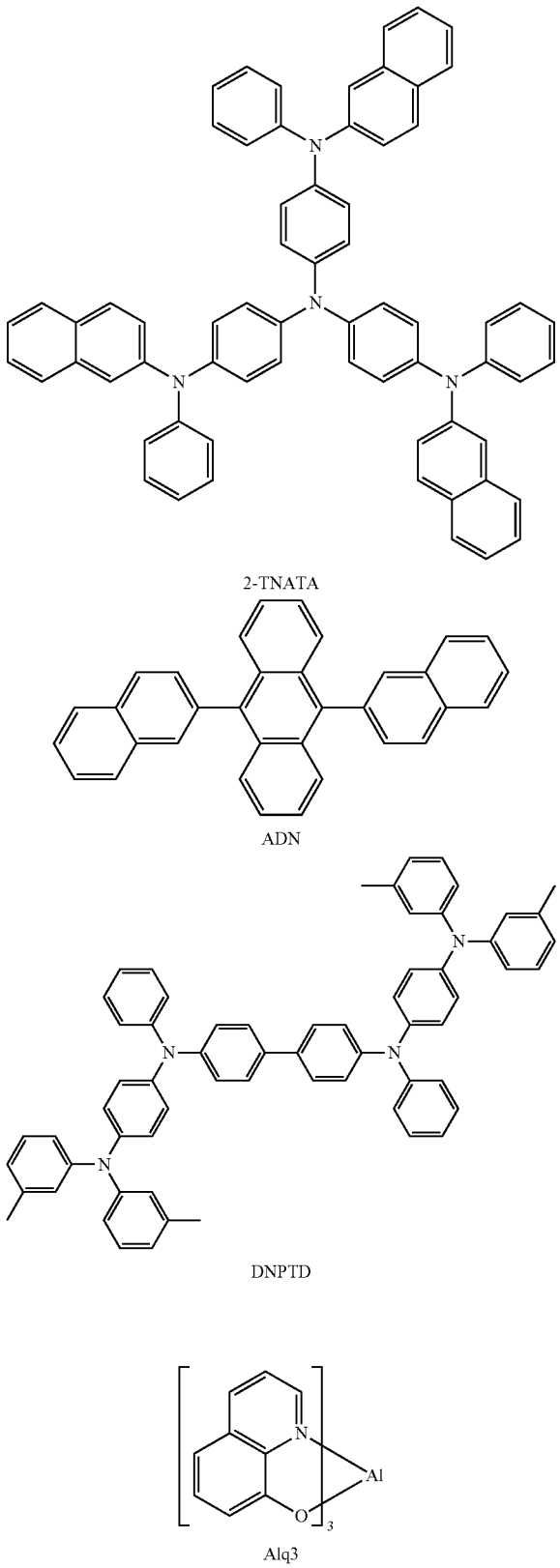

2-TNATA

ADN

DNPTD

Alq3

-continued

Compound 1

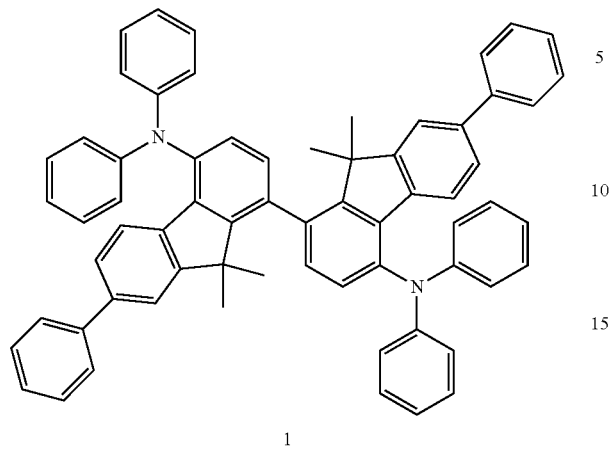

1

TABLE 1

| | Hole injection layer (HIL) | Hole transport layer (HTL) | Emission layer | Electron transport layer (ETL) | Electron injection layer (EIL) | Cathode |
|---|---|---|---|---|---|---|
| Material | 2-TNATA | Compound 1 | ADN (host) + DNTPD (dopant) | Alq3 | LiF | Al |
| Thickness (Å) | 600 | 150 | 285 (host) + 15 (dopant) | 250 | 10 | 2,000 |
| Deposition temperature (° C.) | 330-340 | 240-250 | 260-270 (host) 240-250 (dopant) | 330-340 | 380-400 | 1200 |
| Vacuum degree (torr) | $4.9 \times 10^{-7}$ | $4.9 \times 10^{-7}$ | $4.2 \times 10^{-7}$ | $4.1 \times 10^{-7}$ | $4.6 \times 10^{-7}$ | $4.3 \times 10^{-7}$ |

Example 2

An organic light emitting diode device was manufactured according to the same method as Example 1 except for using Compound 4 instead of Compound 1 to form the hole transport layer (HTL).

Example 3

An organic light emitting diode device was manufactured according to the same method as Example 1 except for using Compound 5 instead of Compound 1 to form the hole transport layer (HTL).

Compound 4

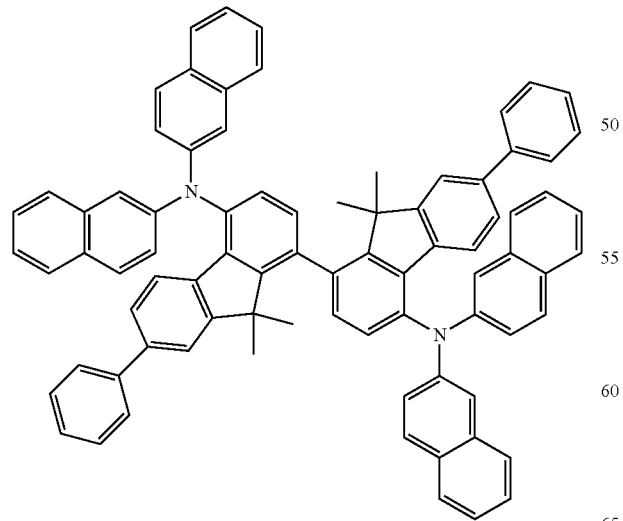

4

Compound 5

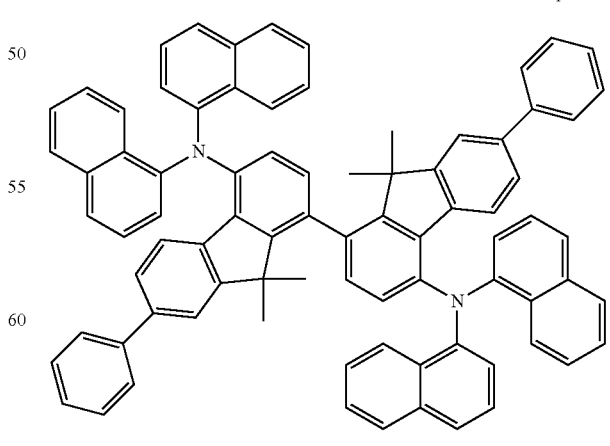

5

Example 4

An organic light emitting diode device was manufactured according to the same method as Example 1 except for using Compound 6 instead of Compound 1 to form the hole transport layer (HTL).

Example 5

An organic light emitting diode device was manufactured according to the same method as Example 1 except for using Compound 10 instead of Compound 1 to form the hole transport layer (HTL).

Example 6

An organic light emitting diode device was manufactured according to the same method as Example 1 except for using Compound 18 instead of Compound 1 to form the hole transport layer (HTL).

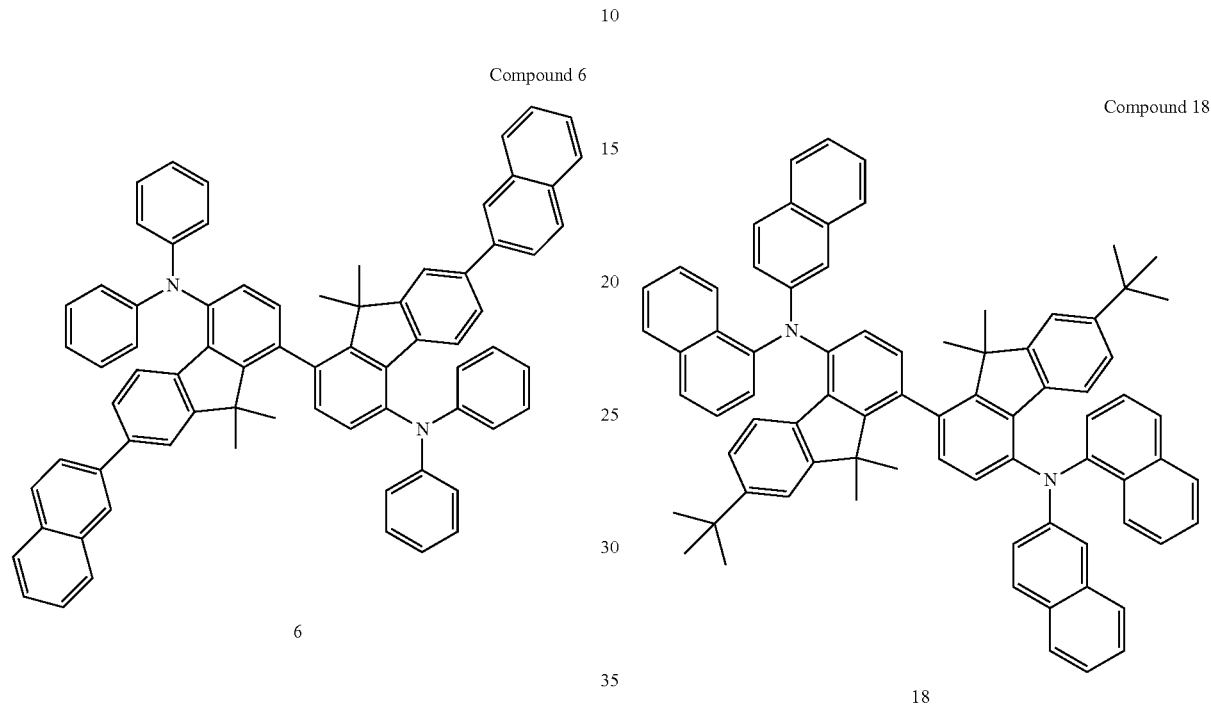

Comparative Example 1

An organic light emitting diode device was manufactured according to the same method as Example 1 except for using NPB instead of Compound 1 to form the hole transport layer (HTL) and depositing the electron transport layer (ETL) at a temperature ranging 260 to 270° C. (an internal pressure under a vacuum condition: $4.1 \times 10^{-7}$ torr). The structure of the organic light emitting diode device according to Comparative Example 1 was provided in Table 2.

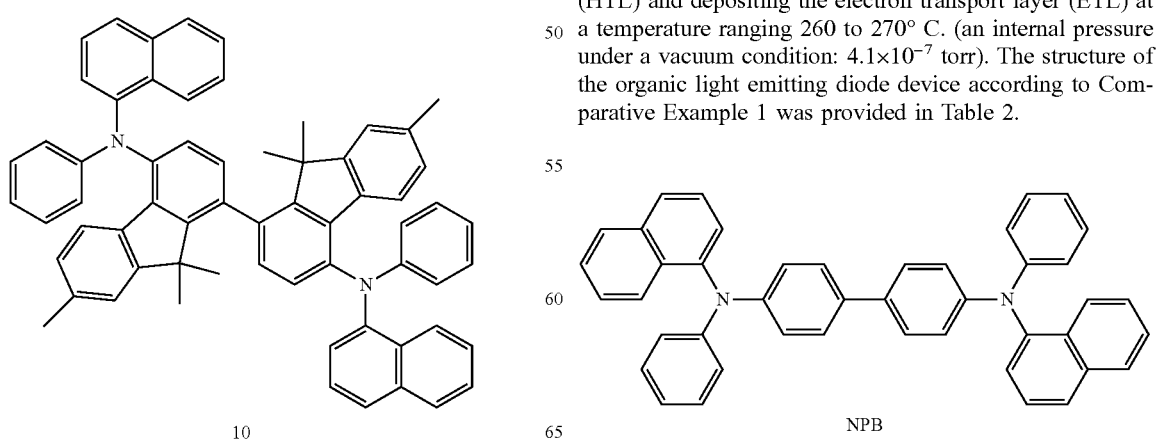

TABLE 2

| | Hole injection layer (HIL) | Hole transport layer (HTL) | Emission layer | Electron transport layer (ETL) | Electron injection layer (EIL) | Cathode |
|---|---|---|---|---|---|---|
| Material | 2-TNATA | NPB | AND (host) + DNTPD (dopant) | Alq3 | LiF | Al |
| Thickness (Å) | 600 | 150 | 285 (host) + 15 (dopant) | 250 | 10 | 2,000 |
| Deposition temperature (° C.) | 330-340 | 240-250 | 260-270 (host) 240-250 (dopant) | 260-270 | 380-400 | 1200 |
| Vacuum degree (torr) | $4.9 \times 10^{-7}$ | $4.9 \times 10^{-7}$ | $4.2 \times 10^{-7}$ | $5.7 \times 10^{-7}$ | $4.6 \times 10^{-7}$ | $4.3 \times 10^{-7}$ |

Evaluation

Characteristics of the organic light emitting diode devices according to Examples 1 to 6 and Comparative Example 1 were evaluated. Driving voltage, current density, luminance, luminous efficiency, and power efficiency of the organic light emitting diodes were evaluated by using a SR3 Spectroscan Source Measurement Unit made by Topcon Co., and the current and voltage of the organic light emitting diodes were evaluated by using SMU 2635A made by Keithley Inc. The results are provided in Table 3.

TABLE 3

| | Hole transport material | Driving voltage (V) | Current density (mA/cm$^2$) | Luminance (cd/m$^2$) | Luminous efficiency (cd/A) | Power efficiency (lm/W) |
|---|---|---|---|---|---|---|
| Example 1 | Compound 1 | 5.1 | 10 | 623 | 6.2 | 3.8 |
| Example 2 | Compound 4 | 5.0 | 10 | 642 | 6.4 | 3.9 |
| Example 3 | Compound 5 | 4.8 | 10 | 651 | 6.5 | 4.0 |
| Example 4 | Compound 6 | 4.8 | 10 | 650 | 6.5 | 4.0 |
| Example 5 | Compound 10 | 5.2 | 10 | 640 | 6.3 | 3.9 |
| Example 6 | Compound 18 | 4.6 | 10 | 694 | 6.7 | 4.2 |
| Comparative Example 1 | NPB | 5.7 | 10 | 600 | 6.0 | 3.3 |

Referring to Table 3, the organic light emitting diode devices according to Examples 1 to 6 showed improved driving voltage, luminance, and efficiency characteristics compared with the organic light emitting diode device according to Comparative Example 1.

By way of summation and review, to provide a reduced size and thickness of a monitor, a television, or the like, cathode ray tubes (CRT) have been replaced with a liquid crystal display (LCD). However, the liquid crystal display (LCD) may require a separate backlight as a non-emissive device may have limitations in terms of a response speed, a viewing angle, and the like.

Recently, as a display device to overcome such limitations, an organic light emitting diode device has been developed. The organic light emitting diode device is a self-light emitting display device having a wide viewing angle, improved contrast, and a fast response time.

The organic light emitting diode device emits a light when electrons injected from one electrode are combined with holes injected from the other electrode and thus, form excitons and emit energy.

Embodiments provide an organic compound applicable to an organic light emitting diode device. Embodiments also provide an organic light emitting diode device including the organic compound. Embodiments also provide a display device including the organic light emitting diode device.

The organic compound according to embodiments may have electrical stability and high charge transport capability, a high glass transition temperature and capability of preventing crystallization.

An organic light emitting diode device including the organic compound according to embodiments may have excellent luminance and life-span characteristics, and high luminous efficiency at a low driving voltage.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope thereof as set forth in the following claims.

What is claimed is:

1. A compound represented by the following Chemical Formula 1:

[Chemical Formula 1]

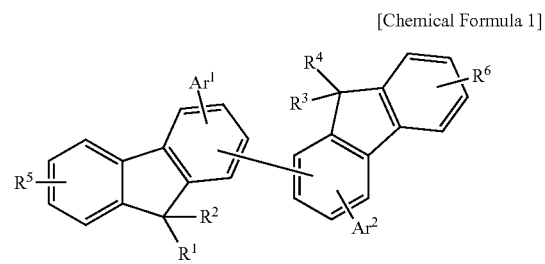

wherein, in the above Chemical Formula 1, $R^1$ to $R^6$ are each independently hydrogen, deuterium, a halogen, a substituted or unsubstituted C1 to C30 alkyl group, a substituted or unsubstituted C2 to C30 alkenyl group, a substituted or unsubstituted C2 to C30 alkynyl group, a substituted or unsubstituted C3 to C30 cycloalkyl group, a substituted or unsubstituted C1 to C30 alkoxy group, a substituted or unsubstituted C6 to C30 aryloxy group, a substituted or unsubstituted C6 to C30 arylthiol group, a substituted or unsubstituted C6 to C30 aryl group, a substituted or unsubstituted C2 to C30 heteroaryl group, a substituted or unsubstituted C1 to C30 amine group, a substituted or unsubstituted silyl group, a cyano group, a nitro group, a hydroxy group, a carboxyl group, or a combination thereof, and $Ar^1$ and $Ar^2$ are each independently a C1 to C30 amine group substituted with an aryl group.

2. The compound as claimed in claim 1, wherein the compound represented by the above Chemical Formula 1 is a compound represented by the following Chemical Formula 2:

[Chemical Formula 2]

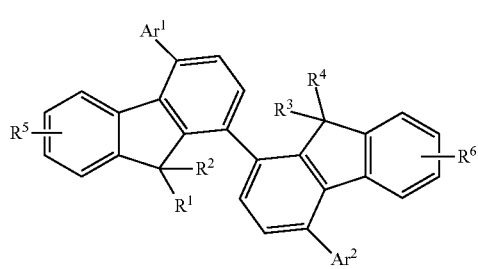

wherein, in the above Chemical Formula 2, $R^1$ to $R^6$ are each independently hydrogen, deuterium, a halogen, a substituted or unsubstituted C1 to C30 alkyl group, a substituted or unsubstituted C2 to C30 alkenyl group, a substituted or unsubstituted C2 to C30 alkynyl group, a substituted or unsubstituted C3 to C30 cycloalkyl group, a substituted or unsubstituted C1 to C30 alkoxy group, a substituted or unsubstituted C6 to C30 aryloxy group, a substituted or unsubstituted C6 to C30 arylthiol group, a substituted or unsubstituted C6 to C30 aryl group, a substituted or unsubstituted C2 to C30 heteroaryl group, a substituted or unsubstituted C1 to C30 amine group, a substituted or unsubstituted silyl group, a cyano group, a nitro group, a hydroxy group, a carboxyl group, or a combination thereof, and $Ar^1$ and $Ar^2$ are each independently a C1 to C30 amine group substituted with a substituted or unsubstituted phenyl group, a substituted or unsubstituted biphenyl group, a substituted or unsubstituted naphthyl group, a substituted or unsubstituted anthracenyl group, or a substituted or unsubstituted phenanthrenyl group.

3. The compound as claimed in claim 1, wherein $Ar^1$ and $Ar^2$ are each independently a C1 to C30 amine group substituted with a substituted or unsubstituted phenyl group, a substituted or unsubstituted biphenyl group, a substituted or unsubstituted naphthyl group, a substituted or unsubstituted anthracenyl group, or a substituted or unsubstituted phenanthrenyl group.

4. The compound as claimed in claim 1, wherein $Ar^1$ and $Ar^2$ are the same.

5. The compound as claimed in claim 1, wherein $R^1$ to $R^6$ are each independently a substituted or unsubstituted C1 to C30 alkyl group, a substituted or unsubstituted C6 to C30 aryl group, or a substituted or unsubstituted C2 to C30 heteroaryl group.

6. The compound as claimed in claim 1, wherein $R^1$ to $R^4$ are each independently a substituted or unsubstituted C1 to C30 alkyl group.

7. The compound as claimed in claim 1, wherein the compound represented by the above Chemical Formula 1 is at least one of the following compounds 1 to 18:

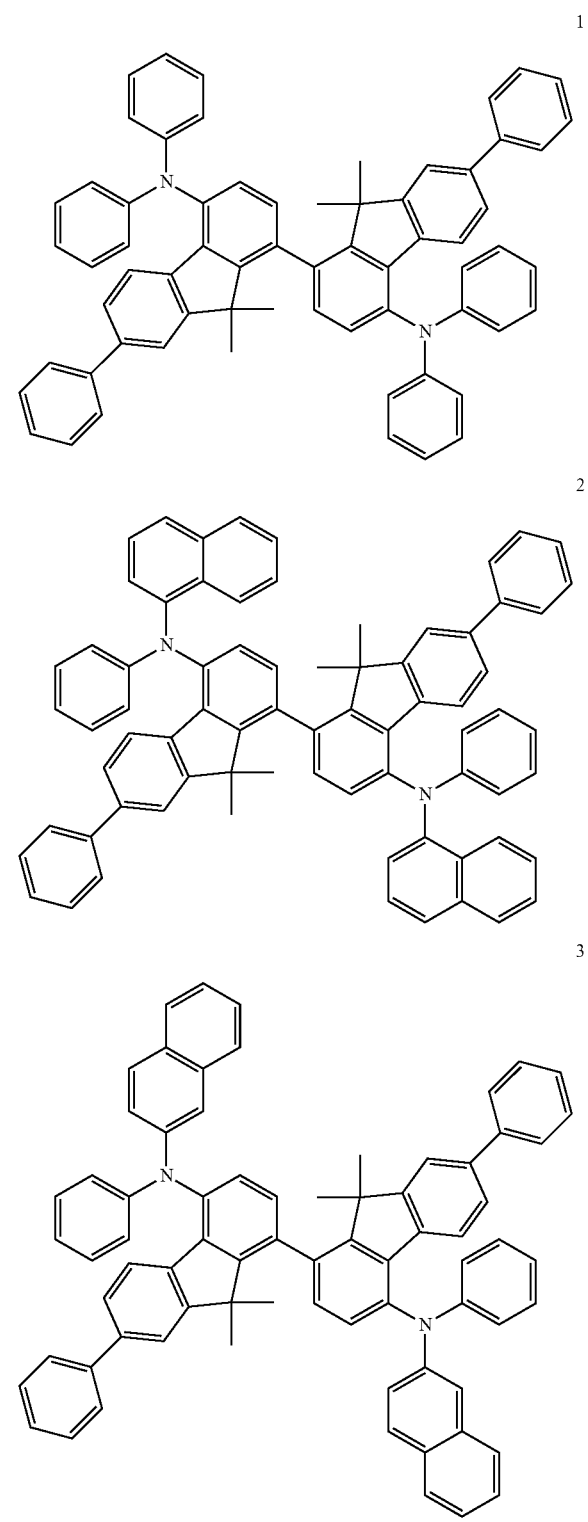

4
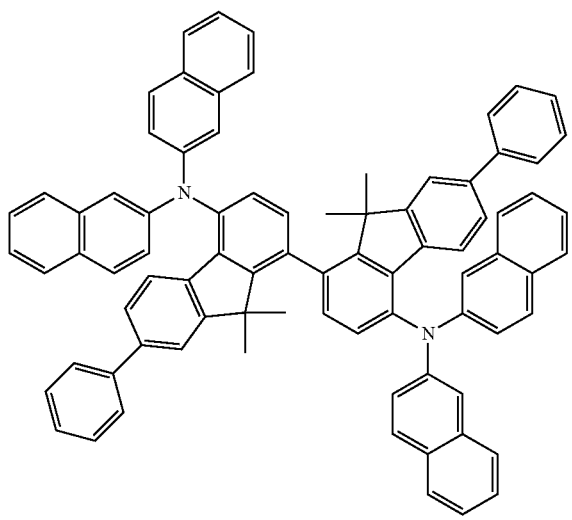
5
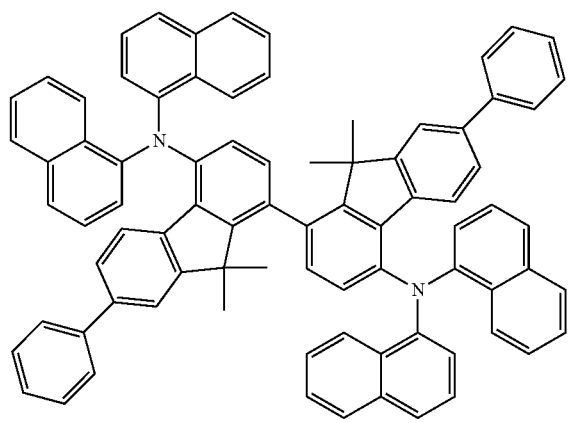
6
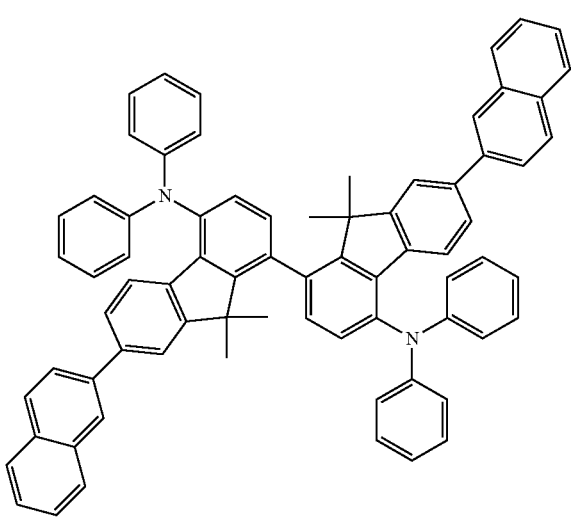
7
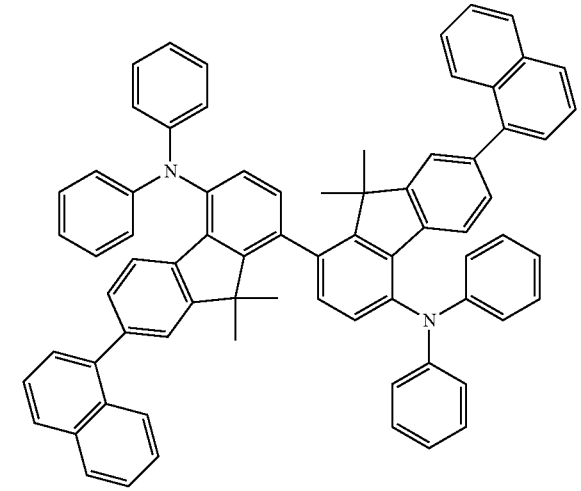
8
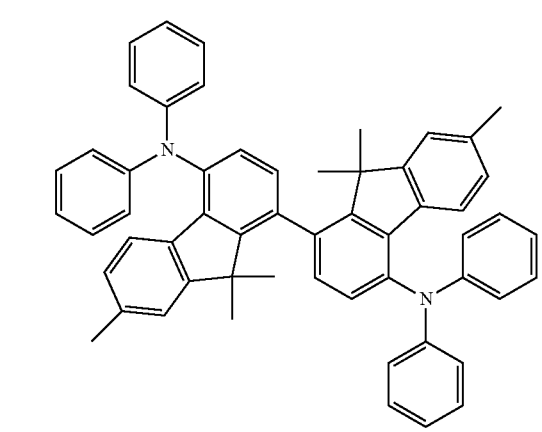
9
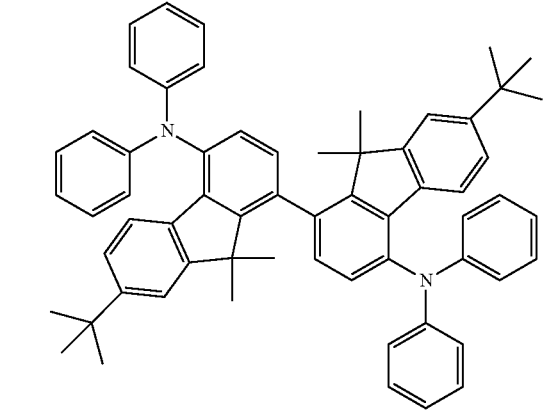

10
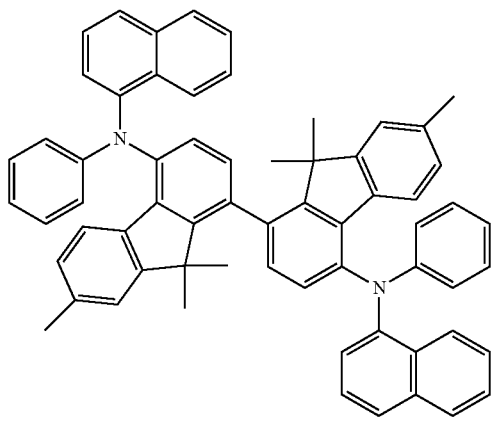
11
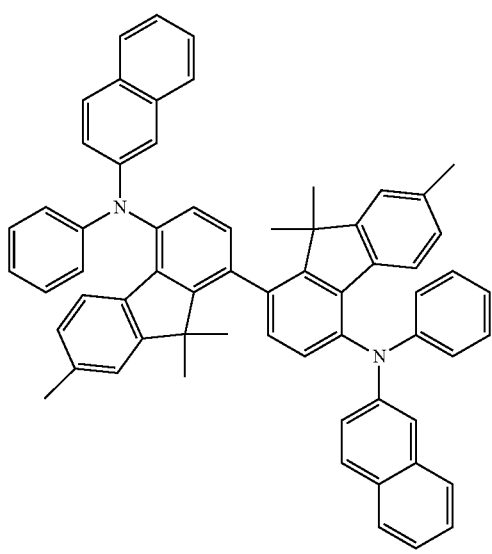
12
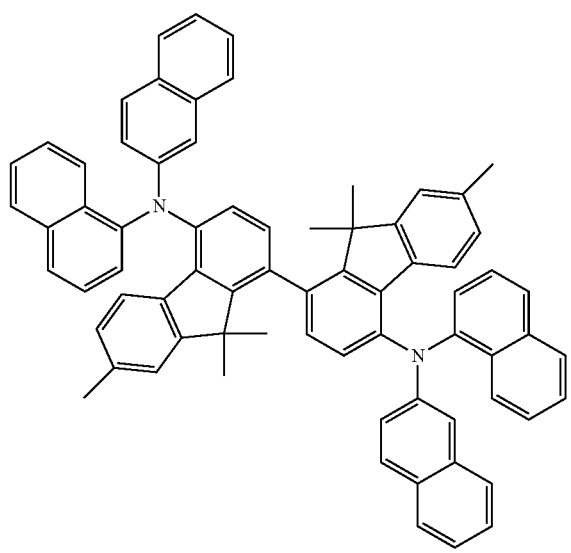
13
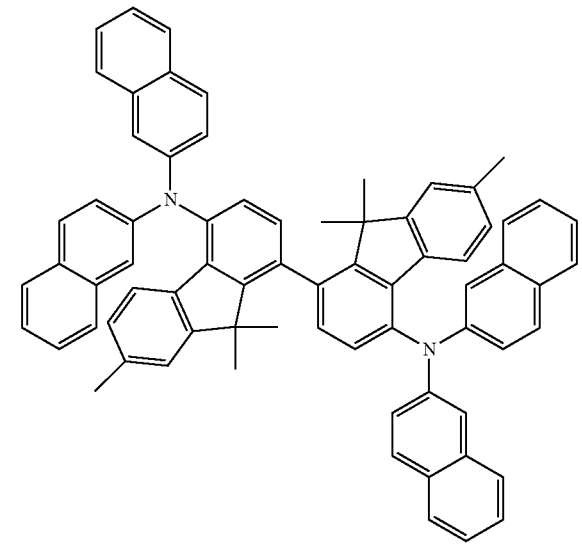
14
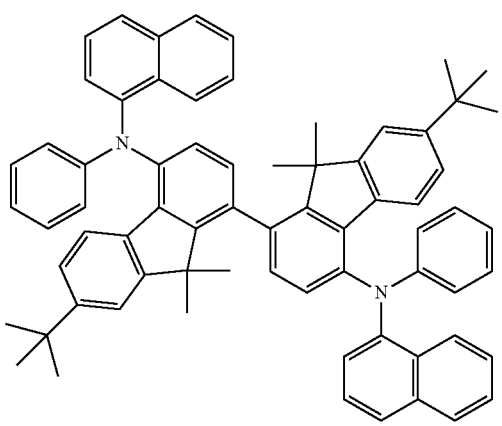
15
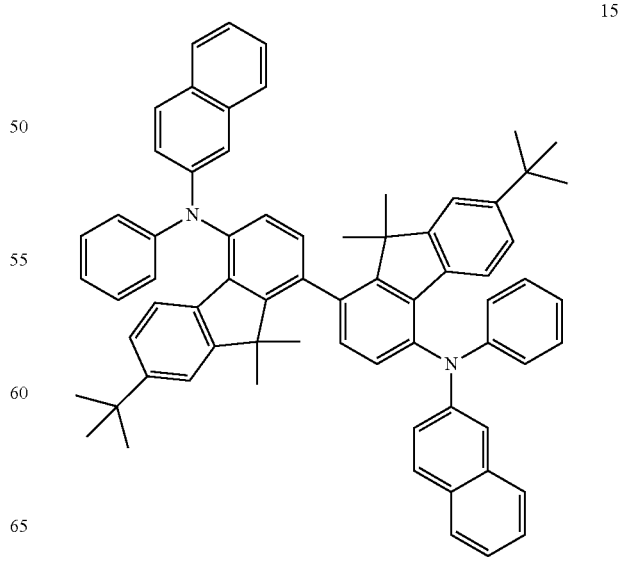

16

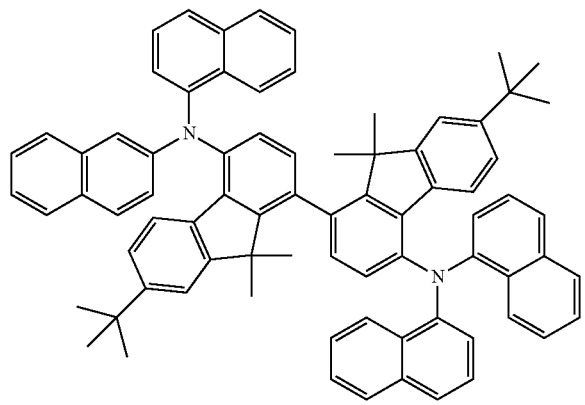

18

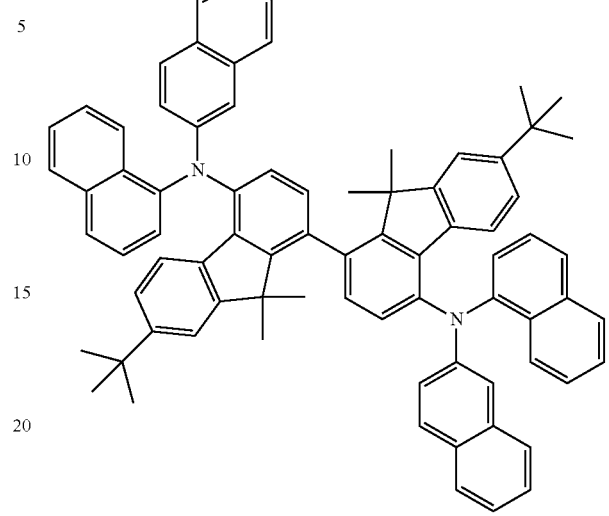

17

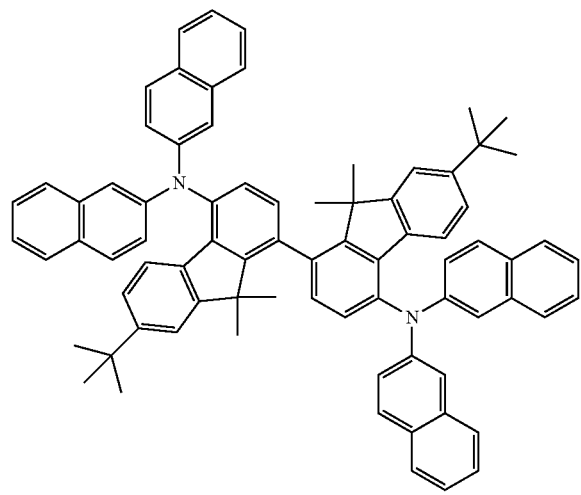

8. An organic light emitting diode device, comprising
an anode,
a cathode, and
an organic layer between the anode and the cathode,
wherein the organic layer includes the compound represented by Chemical Formula 1 as claimed in claim 1.

9. The organic light emitting diode device as claimed in claim 8, wherein the organic layer including the compound represented by Chemical Formula 1 is an electron injection layer (EIL), an electron transport layer (ETL), a hole injection layer (HIL), a hole transport layer (HTL), or an emission layer.

10. The organic light emitting diode device as claimed in claim 8, wherein the organic layer including the compound represented by Chemical Formula 1 is a hole injection layer (HIL) or a hole transport layer (HTL).

11. A display device comprising the organic light emitting diode device as claimed in claim 8.

\* \* \* \* \*